United States Patent [19]
Bold et al.

[11] Patent Number: 5,409,927
[45] Date of Patent: Apr. 25, 1995

[54] MORPHOLIN- AND THIOMORPHOLIN-4-YLAMIDES

[75] Inventors: Guido Bold, Gipf-Oberfrick; Alexander Fässler, Ittigen, both of Switzerland; Marc Lang, Mulhouse, France; Peter Schneider, Bottmingen, Switzerland

[73] Assignee: Ciba-Geigy Corporation, Ardsley, N.Y.

[21] Appl. No.: 36,748

[22] Filed: Mar. 25, 1993

[30] Foreign Application Priority Data

Apr. 1, 1992 [CH] Switzerland ............ 1052/92

[51] Int. Cl.$^6$ ............ A61K 31/535; C07D 265/30
[52] U.S. Cl. ............ 514/237.5; 544/162; 544/168; 544/169
[58] Field of Search ............ 544/168, 169, 162; 514/237.5, 237.8, 934, 18, 19

[56] References Cited

U.S. PATENT DOCUMENTS

| | | | |
|---|---|---|---|
| 4,713,445 | 12/1987 | Szelke et al. | 530/330 |
| 5,095,006 | 3/1992 | Bender et al. | 514/19 |
| 5,242,903 | 9/1993 | Bender et al. | 514/18 |

FOREIGN PATENT DOCUMENTS

| | | |
|---|---|---|
| 0173481 | 3/1986 | European Pat. Off. |
| 0212903 | 3/1987 | European Pat. Off. |
| 0337714 | 10/1989 | European Pat. Off. |
| 0356223 | 2/1990 | European Pat. Off. |
| 0374097 | 6/1990 | European Pat. Off. |
| 0374098 | 6/1990 | European Pat. Off. |
| 0386611 | 9/1990 | European Pat. Off. |
| 0401675 | 12/1990 | European Pat. Off. |
| 0412350 | 2/1991 | European Pat. Off. |
| 0459465 | 12/1991 | European Pat. Off. |
| 0487270 | 5/1992 | European Pat. Off. |
| 899558 | 8/1990 | South Africa . |
| 899559 | 8/1990 | South Africa . |
| 914136 | 2/1992 | South Africa . |
| 8403044 | 8/1984 | WIPO . |
| 8702986 | 5/1987 | WIPO . |
| 02374 | 4/1988 | WIPO . |
| 9106561 | 5/1991 | WIPO . |

OTHER PUBLICATIONS 89-257293/36. Derwent Abstract Corresponding to EP330-925-A-Merck Patent GmbH 1989.
Herold et al. "A Versatile and Stereo Controlled Synthesis of Hydroxyethylene Dipeptide/Sosteres" J. Organ. Chem. 54, 1178-1185, 1989.
European Patent Office Search Report Nov. 10, 1993.

*Primary Examiner*—Shailendra Kumar
*Attorney, Agent, or Firm*—Irving M. Fishman; Karen G. Kaiser

[57] ABSTRACT

There are described compounds of formula I

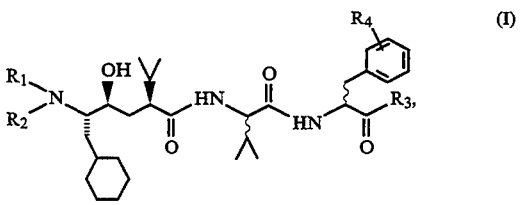

wherein
  $R_1$ is hydrogen or lower alkyl,
  $R_2$ is hydrogen, lower alkyl, lower alkoxycarbonyl, phenyl- or naphthyl-lower alkoxycarbonyl, heterocyclylcarbonyl wherein heterocyclyl contains 5 or 6 ring atoms, is saturated and is bonded to the carbonyl group via a ring nitrogen atom and, in addition to the bonding nitrogen atom, contains as ring member one or more further hetero atoms selected from unsubstituted or $C_1$–$C_4$alkyl-substituted NH, O, S, S=O and $SO_2$, or is lower alkanoyl, phenyl- or naphthyl-lower alkanoyl or lower alkanesulfonyl,
  $R_3$ is morpholino, thiomorpholino, S-oxothiomorpholino or S,S-dioxothiomorpholino, the heterocyclyl radical in heterocyclylcarbonyl $R_2$ having the same definition as $R_3$ or having a definition other than $R_3$, and
  $R_4$ is hydrogen, hydroxy, $C_1$–$C_4$alkoxy, cyano, trifluoromethyl or fluorine, and salts of those compounds where salt-forming groups are present. These compounds are inhibitors of HIV-protease and are used in the treatment of ADS.

4 Claims, No Drawings

MORPHOLIN- AND THIOMORPHOLIN-4-YLAMIDES

The invention relates to non-hydrolysable analogues of peptides that are cleavable by aspartate proteases, namely 5-amino-4-hydroxy-hexanoyl-valyl-phenylalanyl derivatives, to processes for the preparation thereof, to pharmaceutical compositions comprising those peptide analogues, and to the use thereof as medicaments or for the preparation of pharmaceutical compositions for combating diseases caused by retroviruses.

According to present knowledge, ADS is a disease of the immune system caused by the retrovirus HIV (Human Immunodeficiency Virus) which is a member of the lentiviruses. This disease is estimated by the WHO to affect about 10 million people and is continuing to spread. The disease virtually always results in the death of the patient. At present it is not possible to give effective treatment leading to a cure.

AIDS is associated with a selective reduction in T4-helper/inducer. lymphocytes, which is rendered more serious by complications, such as opportunistic infections, resulting from the reduced efficiency of the immune system.

Hitherto, the retroviruses HIV-1 and HIV-2 (HIV stands for Human Immunodeficiency Virus) have been identified as an etiological agent for the disease and have been characterised molecular-biologically.

Therapeutic treatment methods are based especially on the molecular-biological findings. Particular interest is accorded to the search for preparations which impair the replication of the virus itself but do not damage the intact cells and tissues of the patient. Up until now, only inhibitors of reverse transcriptase, an enzyme specific for HIV which is necessary for passing on the genotype of HIV, are available as therapeutic agents or are at an advanced stage of testing, for example AZT (azidothymidine). That compound has a large number of serious side-effects, however.

A more recent procedure has the aim of finding compounds that block replication of the virus by hindering the assembly of infectious .virus particles. This is made possible by inhibiting the normal processing of viral proteins required for maturation of the virus by using certain chemotherapeutic drugs.

HIV-1 and HIV-2 each has in its genome a region that codes for an HIV-protease. That HIV-protease is responsible for the correct proteolytic cleavage of the precursor proteins that arise from the regions of the genome coding for the group specific antigens (gag) and viral enzymes (pol). In that cleavage inter alia the structural proteins of the virus core are freed. The HIV-protease itself is a constituent of the precursor protein encoded by the pol-genome region of HIV-1 and HIV-2, which protein also contains the regions for the reverse transcriptase and the integrase and is thought to be cleaved autoproteolytically.

The HIV-protease cleaves the major core protein p24 of HIV- 1 and HIV-2 preferentially N-terminally of proline radicals, for example in the bivalent radicals Phe-Pro, Leu-Pro or Tyr-Pro. It is a protease having a catalytically active aspartate residue in the active centre, a so-called aspartate protease.

On the basis of the central role of the HIV-protease in the processing of the said core proteins, it is assumed that effective inhibition of that enzyme in vivo will suppress the assembly of mature virions, so that corresponding inhibitors can be used therapeutically.

A prerequisite of therapeutic activity in vivo is the achievement of good inhibition of virus replication in cell experiments and good bioavailability, for example a high level in the blood, in order thus to achieve sufficiently high concentrations in infected cells in the body.

The aim of the present invention is to provide novel inhibitors of retroviral proteases, especially the HIV-1 aspartate protease, which substances contain a peptide isoster not cleavable by such a protease, especially HIV-1 protease, are highly effective in cell experiments even in low concentrations, and on oral or parenteral administration attain concentrations in the blood such that, on the basis of the effective concentrations determined in cell experiments, it is possible to expect in vivo activity against retroviruses, especially HIV and more especially HIV-1. Those compounds are accordingly to be regarded as therapeutic drugs for the mentioned diseases.

The compounds according to the invention are compounds of formula I

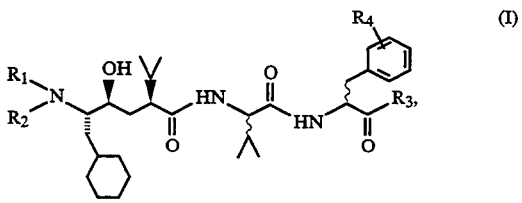

wherein $R_1$ is hydrogen or lower alkyl, $R_2$ is hydrogen, lower alkyl, lower alkoxycarbonyl, phenyl- or naphthyl-lower alkoxycarbonyl, heterocyclylcarbonyl wherein heterocyclyl contains 5 or 6 ring atoms, is saturated and is bonded to the carbonyl group via a ring nitrogen atom and, in addition to the bonding nitrogen atom, contains as ring member one or more further hetero atoms selected from unsubstituted or $C_1$–$C_4$alkyl-substituted NH, O, S, S=O and $SO_2$, or is lower alkanoyl, phenyl- or naphthyl-lower alkanoyl or lower alkanesulfonyl, $R_3$ is morpholino, thiomorpholino, S-oxothiomorpholino or S,S-dioxothiomorpholino, the heterocyclyl radical in heterocyclylcarbonyl $R_2$ having the same definition as $R_3$ or having a definition other than $R_3$, and $R_4$ is hydrogen, hydroxy, $C_1$–$C_4$alkoxy, cyano, trifluoromethyl or fluorine, and salts of those compounds where salt-forming groups are present.

In the description of the present invention, unless expressly defined otherwise the term "lower" used in the definition of groups or radicals, for example lower alkyl, lower alkoxycarbonyl etc., means that the groups or radicals so defined contain up to and including 7 and preferably up to and including 4 carbon atoms and, where there are three or more carbon atoms, may be straight-chain or branched.

Asymmetric carbon atoms in substituents $R_1$ and $R_2$ or the carbon atoms linked to their substituents by wavy bonds in formula I are, independently of one another, in the (R)-, (S)- or (R,S)-configuration. Accordingly, the present compounds may be in the form of mixtures of isomers or in the form of pure isomers, especially mixtures of diastereoisomers, pairs of enantiomers, or pure enantiomers.

The general terms and names used in the description of the present invention preferably have the following definitions, it being possible to use instead of the general definitions any combinations of or individual radicals from the definitions of radicals mentioned hereinabove and hereinbelow.

Lower alkyl $R_1$ or $R_2$ is a straight-chain or branched-chain radical, for example methyl, ethyl, n-propyl, isopropyl, n-butyl, sec-butyl, tert-butyl, pentyl, such as isopentyl, neopentyl, hexyl, such as n-hexyl, or heptyl, such as n-heptyl, $R_1$ and $R_2$ being different or identical. Preferably $R_1$ is hydrogen and $R_2$ is lower alkyl, especially methyl, ethyl or tert-butyl, or lower alkyl $R_1$ and $R_2$ are identical, for example methyl or ethyl.

Lower alkoxycarbonyl $R_2$ preferably contains a branched lower alkyl radical, especially a sec- or tert-lower alkyl radical, and is, for example, butoxycarbonyl, such as tert-butoxycarbonyl or isobutoxycarbonyl. Tert-butoxycarbonyl is especially preferred.

Phenyl-lower alkoxycarbonyl $R_2$ preferably contains a phenyl radical bonded terminally to the lower alkyl radical and is, for example, benzyloxycarbonyl.

Naphthyl-lower alkoxycarbonyl $R_2$ preferably contains a naphthyl radical bonded terminally to the lower alkyl radical and is, for example, 1- or 2-naphthyloxycarbonyl.

Heterocyclyl in heterocyclylcarbonyl $R_2$ that contains 5 or 6 ring atoms, is saturated and is bonded to the carbonyl group via a ring nitrogen atom and, in addition to the bonding nitrogen atom, contains as ring member one or more, preferably up to three, further hetero atoms selected from unsubstituted or $C_1$–$C_4$alkyl-substituted NH, O, S, S=O and $SO_2$, and is preferably imidazol-1-yl, piperazino, N-$C_1$–$C_4$alkyl-piperazino, for example N-methyl- or N-ethyl-piperazino, N-bonded triazolyl, for example N-bonded 1,2,3- or 1,2,4-triazolyl, N-bonded tetrazolyl, for example tetrazol-1-yl or -2-yl, morpholino, thiomorpholino, S-oxothiomorpholino or S,S-dioxothiomorpholino. Morpholinocarbonyl is especially preferred as heterocyclylcarbonyl $R_2$.

Lower alkanoyl $R_2$ is branched or unbranched and is, for example, acetyl, propionyl or n-butyryl, and also pivaloyl, hexanoyl or heptanoyl.

Phenyl-lower alkanoyl $R_2$ contains lower alkanoyl, as defined under lower alkanoyl $R_2$, that is preferably terminally substituted by phenyl, and is, for example, phenylacetyl and also benzoyl.

Naphthyl-lower alkanoyl $R_2$ contains lower alkanoyl, as defined under lower alkanoyl $R_2$, that is preferably terminally substituted by 1- or 2-naphthyl, for example 1- or 2-naphthylacetyl or 1- or 2-naphthoyl.

Lower alkanesulfonyl $R_2$ contains lower alkyl, as defined above for $R_1$ or $R_2$, and is, for example, methane- or ethane-sulfonyl.

$R_3$ is morpholino, thiomorpholino, S-oxothiomorpholino or S,S-dioxothiomorpholino, preferably morpholino or thiomorpholino. Morpholino is especially preferred as heterocyclyl $R_3$.

The heterocyclyl radical in heterocyclylcarbonyl $R_2$ is preferably the same as $R_3$, but may also be different.

The substituent $R_4$ is bonded to the phenyl ring in the o-, m- or p-position, preferably in the o- or p-position and especially in the p-position, and is in a preferred form hydrogen, $C_1$–$C_4$alkoxy, cyano or fluorine, preferably hydrogen.

$C_1$–$C_4$Alkoxy $R_4$ is preferably methoxy or ethoxy.

Salts of compounds of formula I are especially acid addition salts, salts with bases or, where several salt-forming groups are present, optionally also mixed salts or internal salts.

Salts are especially the pharmaceutically acceptable salts of compounds of formula I that are non-toxic when used in the correct dose.

Such salts are formed, for example, from compounds of formula I having one or more acidic groups, for example a carboxy group, and are, for example, the salts thereof with suitable bases, such as non-toxic metal salts derived from metals of groups Ia, Ib, IIa and IIb of the Periodic Table of Elements, especially suitable alkali metal salts, for example lithium, sodium or potassium salts, or alkaline earth metal salts, for example magnesium or calcium salts, and also zinc salts or ammonium salts, as well as those salts which are formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)-amines, such as mono-, bis- or tris-( 2-hydroxyethyl)-amine, 2-hydroxy-tert-butylamine or tris(hydroxymethyl)methylamine, N,N-di-lower alkyl-N-(hydroxy-lower alkyl)-amines, such as N,N-dimethyl-N-(2-hydroxyethyl)-amine or tris(2-hydroxyethyl)amine, N-methyl-D-glucamine or quaternary ammonium salts, such as tetrabutylammonium salts. The compounds of formula I having one or more basic groups, for example an amino or imino group, may form acid addition salts, for example with inorganic acids, for example a hydrohalic acid, such as hydrochloric acid, sulfuric acid or phosphoric acid, or with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also with amino acids, for example glutamic acid or aspartic acid, and with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with the formation of cyclamates) or with other acidic organic compounds, such as ascorbic acid. Compounds of formula I having acidic and basic groups may also form internal salts.

For the purposes of isolation and purification it is also possible to use pharmaceutically unacceptable salts.

The compounds of the present invention exhibit inhibitory action on retroviral aspartate proteases, especially activity inhibiting HIV-protease. In the tests described below, in concentrations corresponding to an $IC_{50}$ of from 10 to 1000 nM, especially from 10 to 100 nM, they especially inhibit the action of the HIV-protease of HIV- 1 and are therefore suitable agents against diseases caused by those or related retroviruses, such as against AIDS.

The ability of the compounds of formula I to inhibit the proteolytic activity of, for example, HIV-1-protease can be demonstrated, for example, in accordance with the method described by A. D. Richards et al., J. Biol.

Chem. 265(14), 7733–7736 (1990). In that method there is used as substrate for a recombinant HIV-1-protease (prepared in accordance with Billich, S., et al., J. Biol. Chem. 263(34), 17905–17908 (1990)) a synthetic chromophoric peptide (for example HKARVL[NO$_2$]FEA-NleS (Bachem, Switzerland; see M. W. Pennington et al., Peptides 1990, ed.: E. Girault and D. Andrew (1991), ESCOM Sci. Publ. B. V., p. 787–789) or an icosapeptide such as RRSNQVSQNYPIVQNIQGRR (prepared by peptide synthesis in accordance with known methods: J. Schneider et al., Cell 54, 363–368 (1988)) that corresponds to one of the cleavage sites of the gag-precursor protein. That substrate and cleavage products thereof can be analysed by high pressure liquid chromatography (HPLC).

For example, an inhibitor of formula I to be tested is dissolved in dimethyl sulfoxide; the enzyme test is carried out by adding suitable dilutions of the inhibiting substance in 20 mM β-morpholinoethanesulfonic acid (MES) buffer pH 6.0 to the assay mix comprising the above-mentioned chromophoric peptide (67.2 μM) in 0.3M sodium acetate, 0.1M NaCl pH 7.4 or the above-mentioned icosapeptide (122 μM) in 20 mM MES buffer pH 6.0. The size of each batch is 100 μl. The reaction is started by the addition of in the first case 2 μl and in the second case 10 μl of HIV-1-protease and is stopped in the first case after 15 minutes by the addition of 100 μl of 0.3M HClO$_4$, and in the second case after one hour's incubation at 37° C. by the addition of 10 μl of 0.3M HClO$_4$. After centrifugation of the sample for 5 minutes at 10,000×g in 100 μl (batch with chromophoric peptide) or 20 μl (icosapeptide batch) of the resulting supernatant and after application to a 125×4.6 mm Nucleosil® C18-5μ-HPLC column (Macherey & Nagel, Düren) and elution, the reaction products are quantified with reference to the peak height of the cleavage product at 280 nm (batch with chromophoric peptide) or at 215 nm (batch with icosapeptide), gradient: 100% el.1→50% el./50% el.2 (el.1: 75% acetonitrile, 90% H$_2$O, 0.1% trifluoroacetic acid (TFA); el.2:75% acetonitrile, 25% H$_2$O, 0.08% TFA) in the course of 15 minutes; throughflow rate 1 ml/min.

In that procedure there are determined for compounds of formula I especially IC$_{50}$ values (IC$_{50}$=concentration that reduces the activity of the HIV-1-protease by 50% in comparison with a control without inhibiting substance) of approximately from $10^{-8}$ to $10^{-6}$M, especially from $10^{-8}$ to $10^{-7}$M.

In a further test it can be shown that the compounds of the present invention protect cells that are normally infected by HIV from such an infection or at least retard such an infection. In the test, the human T-cell leukaemia cell line MT-2 (Science 229, 563 (1985)), which is sensitive to the cytopathogenic effect of HIV, is incubated with HIV-1 alone or with HIV-1 in the presence of one of the compounds according to the invention and after several days the viability of the cells thus treated is assessed. For this purpose the MT-2 cells are kept in RPMI 1640 medium (Gibco, Switzerland; RPMI 1640 comprises an amino acid mixture without L-Gln) that has been supplemented with 10% heat-inactivated foetal calf serum, L-glutamine, Hepes (2-[4-(2-hydroxyethyl)-1-piperazino]-ethanesulfonic acid) and standard antibiotics, at 37° C. in humidified air containing 5% CO$_2$.50 gl of the respective test compound in culture medium and 100 μl of HIV-1 in culture medium (800 TCID50/ml) (TCID50=Tissue Culture Infectious Dose 50=dose that infects 50% of the MT-2 cells) are added to 4×10$^3$ exponentially growing MT-2 cells in 50 μl of culture medium per well in 96-well microtitre plates. Parallel batches on a further microliter plate with cells and test compound receive 100 gl of culture medium without the virus. After incubation for 4 days, the reverse transcriptase (RT) activity in 10 μl of the cell supernatant is determined. The RT activity is determined in 50 mM Tris (α,α,α-tris(hydroxymethyl)methylamine, Ultra pur, Merck, Federal Republic of Germany) pH 7.8; 75 mM KCl, 2 mM dithiothreitol, 5 mM MgCl$_2$; 0.05% Nonidet P-40 (detergent; Sigma, Switzerland); 50 μg/ml of polyadenylic acid (Pharmacia, Sweden); 1.6 μg/ml of dT(12-18) (Sigma, Switzerland). The mixture is filtered through a 0.45μ Acrodisc filter (Gelman Sciences Inc, Ann Arbor) and stored at −20° C. 0.1% (v/v) [alpha-$^{32}$P]dTTP is added to aliquots of that solution in order to obtain a final radioactive activity of 10 μCi/ml. 10 μl of the culture supernatant are transferred to a fresh 96-well microtitre plate and 30 μl of the said RT cocktails are added thereto. After mixing, the plate is incubated for from 1.5 to 3 hours at 37° C. 5 μl of that reaction mixture are transferred to DE81-paper (Whatman). The dried filters are washed three times for 5 minutes with 300 mM NaCl/25 mM trisodium citrate and once with 95% ethanol and again dried in the air. Evaluation is made in a Matrix Packard 96-well counter (Packard, Zürich, Switzerland). The ED90 values are calculated and are defined as the lowest concentration of the respective test compound that reduces the RT activity by 90% in comparison with cell batches not treated with the test compound. The RT activity is a measure of the replication of HIV-1.

In that test the compounds according to the invention especially exhibit an ED90 of from $10^{-8}$ to $10^{-6}$M, especially from $10^{-8}$ to $10^{-7}$M.

The compounds of the present invention exhibit advantageous pharmacokinetic properties, which allow the assumption that they will exhibit the said inhibitory actions in vivo. For example, in the case of intravenous or intraperitoneal administration of 20 mg/kg of one of the mentioned compounds to mice, the blood level 1 hour after administration is approximately the same as or higher than the ED90 in the cell assay.

In the case of peroral administration of 120 mg/kg of one of the said compounds, 30 minutes after administration the concentrations found in the blood of the mice are likewise above the ED90 in the cell assay and preferably constitute approximately 10 times the ED90 in the cell assay.

In order to determine the blood level the following procedure, for example, is carried out: the compounds to be tested are dissolved in a solvent, such as DMSO (dimethyl sulfoxide). A solution of hydroxypropyl-β-cyclodextrin (20% w/v) in water is added until the desired concentration of the active ingredient (for example 2 mg/ml for parenteral administration, 12 mg/ml for oral administration) is obtained while at the same time a concentration of 5% DMSO (v/v) is established. Compounds that are insoluble under these conditions are administered only intraperitoneally, while soluble compounds are also administered intravenously. After administration of the compounds (for example 20 mg/kg intravenously or intraperitoneally, or 120 mg/kg perorally) blood is taken at various times, for example after 30 or 60 minutes. Blood is taken from three mice each time and, either for each mouse individually or from the combined blood of the three mice, the supernatant is obtained after the addition of a solvent, for example acetonitrile, and subsequent centrifugation. The concentration of the active ingredient is measured using HPLC, for example on a Nucleosil® 5C$_{18}$ column (Macherey-Nagel) of 120 mm length and 4.6 mm diameter with either 60% acetonitrile/40% water/0.05% trifluoroacetic acid (v/v) or 50% acetonitrile/40% water/0.05% trifluoroacetic acid (v/v) as eluant (flow rate 1 ml/min) by detection and quantification at 200 nm.

In the groups of compounds of formula I mentioned hereinbelow, it is advantageously possible, for example in order to replace more general definitions by more specific definitions, to use definitions of radicals from the above-mentioned general definitions.

Preference is given to compounds of formula I wherein $R_1$ is hydrogen, $R_2$ is hydrogen, lower alkoxycarbonyl, especially sec- or tert-lower alkoxycarbonyl, for example butoxycarbonyl, such as tert-butoxycarbonyl or isobutoxycarbonyl, more especially tert-butoxycarbonyl, or is heterocyclylcarbonyl wherein heterocyclyl contains 5 or 6 ring atoms, is saturated and is bonded to the carbonyl group via a ring nitrogen atom and, in addition to the bonding nitrogen atom, contains as ring member unsubstituted or $C_1$–$C_4$alkyl-substituted NH, O, S, S=O or $SO_2$, especially piperazinocarbonyl, N-$C_1$–$C_4$alkyl-piperazinocarbonyl, for example N-methyl- or N-ethyl-piperazinocarbonyl, morpholinocarbonyl, thiomorpholinocarbonyl, S-oxothiomorpholinocarbonyl or S,S-dioxothiomorpholinocarbonyl, more especially morpholinocarbonyl, $R_3$ is morpholino, thiomorpholino, S-oxothiomorpholino or S,S-dioxothiomorpholino, especially morpholino or thiomorpholino, more especially morpholino, and $R_4$ is hydrogen, or pharmaceutically acceptable salts of such compounds having salt-forming groups.

Greater preference is given to compounds of formula Ib

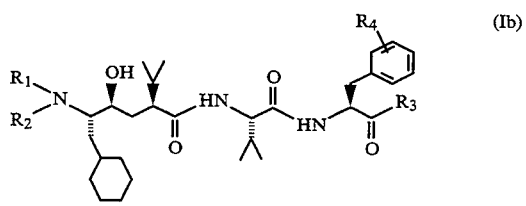

wherein the radicals $R_1$, $R_2$, $R_3$ and $R_4$ are as defined hereinbefore for compounds of formula I, or pharmaceutically acceptable salts of such compounds having salt-forming groups.

Special preference is given to compounds of formula Ib wherein $R_1$ is hydrogen, $R_2$ is hydrogen, lower alkoxycarbonyl, especially sec- or tert-lower alkoxycarbonyl, for example butoxycarbonyl, such as tert-butoxycarbonyl or isobutoxycarbonyl, more especially tert-butoxycarbonyl, or is heterocyclylcarbonyl wherein heterocyclyl contains 5 or 6 ring atoms, is saturated and is bonded to the carbonyl group via a ring nitrogen atom and, in addition to the bonding nitrogen atom, contains as ring member unsubstituted of $C_1$–$C_4$alkyl-substituted NH, O, S, S=O or $SO_2$, especially piperazinocarbonyl, N-$C_1$–$C_4$alkyl-piperazinocarbonyl, for example N-methyl- or N-ethyl-piperazinocarbonyl, morpholinocarbonyl, thiomorpholinocarbonyl, S-oxothiomorpholinocarbonyl or S,S-dioxothiomorpholinocarbonyl, more especially morpholinocarbonyl, $R_3$ is heterocyclyl bonded via a ring nitrogen atom, as defined for heterocyclylcarbonyl $R_3$ above, especially piperazino, N-$C_1$–$C_4$alkyl-piperazino, for example N-methyl- or N-ethyl-piperazino, morpholino, thiomorpholino, S-oxothiomorpholino or S,S-dioxothiomorpholino, more especially morpholino, and $R_4$ is hydrogen, or pharmaceutically acceptable salts of such compounds having salt-forming groups.

Greater preference is given to the compounds of formula Ib wherein $R_1$ is hydrogen, $R_2$ is hydrogen, sec- or tert-lower alkoxycarbonyl, piperazinocarbonyl, N-$C_1$–$C_4$alkylpiperazinocarbonyl, morpholinocarbonyl, thiomorpholinocarbonyl, S-oxothiomorpholinocarbonyl or S,S-dioxothiomorpholinocarbonyl, $R_3$ is morpholino, thiomorpholino, S-oxothiomorpholino or S,S-dioxothiomorpholino, especially morpholino or thiomorpholino, more especially morpholino, and $R_4$ is hydrogen, or pharmaceutically acceptable salts of such compounds having salt-forming groups.

Very special preference is given to the compounds of formula Ib wherein $R_1$ is hydrogen, $R_2$ is lower alkoxycarbonyl, especially sec- or tert-lower alkoxycarbonyl, such as tert-butoxycarbonyl or isobutoxycarbonyl, $R_3$ is morpholino, and $R_4$ is hydrogen.

The invention relates most especially to the compounds mentioned in the Examples or the pharmaceutically acceptable salts of such compounds where salt-forming groups are present.

The compounds of formula I and salts of such compounds having at least one salt-forming group are obtained according to processes known per se, for example as follows:

a) for the preparation of compounds of formula I wherein at least one of the radicals $R_1$ and $R_2$ is lower alkyl and the other is hydrogen or $R_1$ and $R_2$ are both lower alkyl and the remaining radicals are as defined for compounds of formula I, an amino compound of formula II (which corresponds to a compound of formula I wherein $R_1$ and $R_2$ are hydrogen)

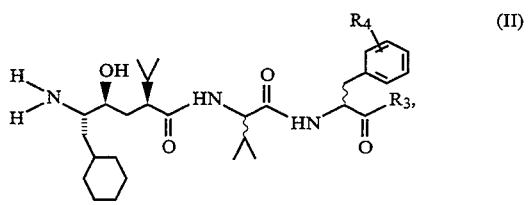

wherein $R_3$ and $R_4$ are as defined for compounds of formula I and wherein free functional groups, with the exception of those participating in the reaction, may if necessary be in protected form, is reacted with an alkylating reagent in order to introduce the lower alkyl radical $R_1$, the lower alkyl radical $R_2$ or the two radicals lower alkyl $R_1$ and lower alkyl $R_2$, and any protecting groups present are removed, or b) for the preparation of a compound of formula I wherein $R_2$ is lower alkoxycarbonyl, phenyl- or naphthyl-lower alkoxycarbonyl, heterocyclylcarbonyl wherein heterocyclyl contains 5 or 6 ring atoms, is saturated and is bonded to the carbonyl group via a ring nitrogen atom and, in addition to the bonding nitrogen atom, contains as ring member unsubstituted or $C_1$–$C_4$alkyl-substituted NH, O, S, S=O or $SO_2$, or is lower alkanoyl, phenyl- or naphthyl-lower alkanoyl or lower alkanesulfonyl, and the remaining radicals are as defined and wherein free functional groups, with the exception of those participating in the reaction, may if necessary be in protected form, an amino compound of formula IV

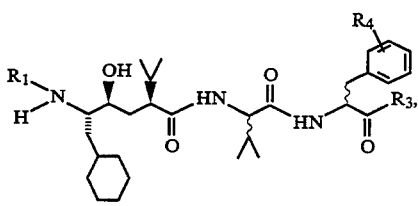

(IV)

wherein the radicals $R_1$, $R_3$ and $R_4$ are as defined for compounds of formula I and wherein free functional groups, with the exception of those participating in the reaction, may if necessary be in protected form, or a reactive amino derivative thereof, is condensed with an acid of formula V $R_2$—OH         (V), wherein $R_2$ is lower alkoxycarbonyl, phenyl- or naphthyl-lower alkoxycarbonyl, heterocyclylcarbonyl wherein heterocyclyl contains 5 or 6 ring atoms, is saturated and is bonded to the carbonyl group via a ring nitrogen atom and, in addition to the bonding nitrogen atom, contains as ring member unsubstituted or $C_1$–$C_4$alkyl-substituted NH, O, S, S=O or $SO_2$, or is lower alkanoyl, phenyl- or naphthyl-lower alkanoyl or lower alkanesulfonyl and wherein free functional groups, with the exception of those participating in the reaction, may if necessary be in protected form, or with a reactive acid derivative thereof, and any protecting groups present are removed, or c) an amino compound of formula VI

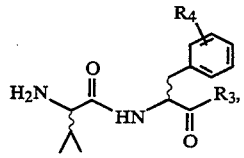

(VI)

wherein $R_3$ and $R_4$ are as defined for compounds of formula I and wherein free functional groups, with the exception of those participating in the reaction, may if necessary be in protected form, or a reactive amino derivative thereof, is condensed with a carboxylic acid of formula VII

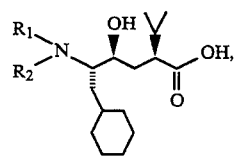

(VII)

wherein the radicals $R_1$ and $R_2$ are as defined for compounds of formula I and wherein free functional groups, with the exception of those participating in the reaction, may if necessary be in protected form, or with a reactive acid derivative thereof, and any protecting groups present are removed, or d) an amino compound of formula VIII

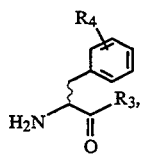

(VIII)

wherein $R_3$ and $R_4$ are as defined for compounds of formula I and wherein free functional groups, with the exception of those participating in the reaction, may if necessary be in protected form, or a reactive amino derivative thereof, is condensed with a carboxylic acid of formula IX

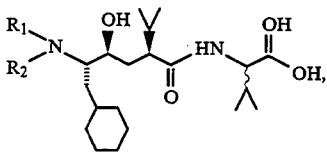

(IX)

wherein $R_1$ and $R_2$ are as defined for compounds of formula I and wherein free functional groups, with the exception of those participating in the reaction, may if necessary be in protected form, or with a reactive acid derivative thereof, and any protecting groups present are removed, or e) a compound of formula X $R_3$—H         (X), wherein $R_3$ is as defined for compounds of formula I and wherein free functional groups, with the exception of those participating in the reaction, may if necessary be in protected form, or a reactive derivative thereof, is condensed with a carboxylic acid of formula XI

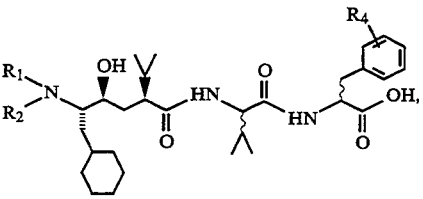

(XI)

wherein $R_1$, $R_2$ and $R_4$ are as defined for compounds of formula I and wherein free functional groups, with the exception of those participating in the reaction, may if necessary be in protected form, or with a reactive acid derivative thereof, and any protecting groups present are removed, and, if desired, a compound of formula I having at least one salt-forming group obtainable in accordance with any one of the above processes a) to e) is convened into a salt or an obtainable salt is converted into the free compound or into a different salt and/or mixtures of isomers of compounds of formula I which may be obtainable am separated and/or a compound of formula I according to the invention is converted into a different compound of formula I according to the invention.

Process a) (Nucleophilic substitution)

In starting materials of formula II, functional groups, with the exception of groups that are intended to participate in the reaction or do not react under the reaction conditions, are protected independently of one another by protecting groups.

An alkylating reagent for the introduction of the lower alkyl radical $R_1$, the lower alkyl radical $R_2$ or the two radicals lower alkyl $R_1$ and lower alkyl $R_2$ is especially selected from the following reagents:

German Offenlegungsschrift 2 331 133 mentions alkylating agents that can be reacted under the reaction conditions mentioned therein with a compound of formula I.

Further alkylating agents are selected from corresponding lower alkyl compounds of formula III

R—Y             (III)

wherein R is a lower alkyl radical corresponding to $R_1$ and/or $R_2$, and Y is a leaving group. A leaving group is especially a nucleofugal leaving group selected from hydroxy esterified by a strong inorganic or organic acid, such as hydroxy esterified by a mineral acid, for example a hydrohalic acid, such as hydrochloric, hydrobromic or hydriodic acid, or by a strong organic sulfonic acid, such as an unsubstituted or substituted, for example halo-substituted, such as fluoro-substituted, lower alkanesulfonic acid or an aromatic sulfonic acid, for example a benzenesulfonic acid that is unsubstituted or substituted by lower alkyl, such as methyl, halogen, such as bromine, and/or by nitro, for example a methanesulfonic, trimethanesulfonic or p-toluenesulfonic acid, or hydroxy esterified by hydrazoic acid.

The reaction may take place under the conditions of a nucleophilic substitution of the first or second order.

For example, a compound of formula III is reacted in a polar aprotic solvent, for example acetone, acetonitrile, nitromethane, dimethyl sulfoxide, hexamethylphosphoric acid triamide or dimethylformamide, with the amino compound of formula II, or the reaction is carried out in a protic solvent, for example an alcohol, such as methanol, ethanol, ethylene glycol or isopropanol, or water which is optionally in admixture with organic solvents, for example ethanol, tetrahydrofuran or acetone, as solubiliser. The reaction is carded out in the absence or presence of catalysts, such as Lewis acids, for example $SnCl_4$, $BF_3$, $AlCl_3$, $FeCl_3$, $ZnCl_2$ or $SbCl_5$, the said Lewis acids preferably being used when Y is a halogen atom. The substitution reaction is optionally carded out at reduced or elevated temperature, for example in a temperature range of from approximately $-40°$ to approximately $120°$ C., preferably from approximately $-10°$ to approximately $100°$ C., and optionally under an inert gas, for example under a nitrogen or argon atmosphere.

The reaction can also be carded out using two different compounds of formula III in sequence, so as to prepare compounds of formula I wherein $R_1$ and $R_2$ are different lower alkyl radicals. This is achieved, for example, by the use of suitable stoichiometric amounts of the starting compounds, for example for the introduction of the first lower alkyl radical by the use of a molar amount of the first compound of formula III that is lower than the molar amount of the compound of formula II, or by the use of suitable amino-protecting groups that are removed after the first alkylation, and subsequent alkylation with a second compound of formula III that carries a lower alkyl radical different from that of the first compound.

The protecting groups for functional groups in starting materials the reaction of which is to be avoided, especially carboxy, amino, imino or hydroxy groups, include especially those protecting groups (conventional protecting groups) which are customarily used in the synthesis of peptide compounds and also in the synthesis of cephalosporins and penicillins and also of nucleic acid derivatives and sugars. Those protecting groups may already be present in the precursors and are intended to protect the functional groups in question against undesirable secondary reactions, such as acylation, etherification, esterification, oxidation, solvolysis etc. In certain cases the protecting groups may also result in the reactions' taking a selective, for example stereoselective, course. It is characteristic of protecting groups that they can be removed readily, that is to say without undesirable secondary reactions taking place, for example by solvolysis, reduction, photolysis, or enzymatically, for example also under physiological conditions, and that they are not present in the end products. Compounds of formula I having protected functional groups may have a higher metabolic stability or pharmacodynamic properties that are better in some other way than the corresponding compounds having free functional groups.

The protection of functional groups by such protecting groups, the protecting groups themselves and reactions for the removal thereof are described, for example, in standard works, such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Vol. 3 (E. Gross and J. Meienhofer, Eds.), Academic Press, London and New York 1981, in "Methoden der organischen Chemie" ("Methods of Organic Chemistry"), Houben-Weyl, 4th Edition, Vol. 15/I, Georg Thieme Verlag, Stuttgart 1974, in H.-D. Jakubke and H. Jescheit, "Aminosäuren, Peptide, Proteine" ("Amino acids, Peptides, Proteins"), Verlag Chemie, Weinheim, Deerfield Beach and Basle 1982, and in Jochen Lehmann, "Chemie der Kohlenhydrate: Monosaccharide und Derivate" ("The Chemistry of the Carbohydrates: Monosaccharides and Derivatives"), Georg Thieme Verlag, Stuttgart 1974.

A carboxy group is protected, for example, in the form of an ester group that is selectively cleavable under mild conditions. A carboxy group protected in esterified form is especially esterified by a lower alkyl group which is preferably branched in the 1-position of the lower alkyl group or substituted by suitable substituents in the 1- or 2-position of the lower alkyl group.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl, or sec-lower alkoxycarbonyl, for example isobutoxycarbonyl.

A protected carboxy group esterified by a lower alkyl group that is substituted by suitable substituents in the 1- or 2-position of the lower alkyl group is, for example, arylmethoxycarbonyl having one or two aryl radicals, wherein aryl is phenyl that is unsubstituted or mono-, di- or tri-substituted, for example, by lower alkyl, for example ten-lower alkyl, such as tert-butyl, lower alkoxy, for example methoxy, hydroxy, halogen, for example chlorine, and/or by nitro, for example benzyloxycarbonyl, benzyloxycarbonyl substituted by the said substituents, for example 4-nitrobenzyloxycarbonyl or 4-methoxybenzyloxycarbonyl, diphenylmethoxycarbonyl or diphenylmethoxycarbonyl substituted by the said substituents, for example di(4-methoxyphenyl)methoxycarbonyl, fluorenylmethoxycarbonyl, and also carboxy esterified by a lower alkyl group, the lower alkyl group being substituted by suitable substituents in the 1- or 2-position, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, and also 2-(trisubstituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-tri-lower alkylsilylethoxycarbonyl, for example 2-trimethylsilylethoxycarbonyl or 2-(di-n-butyl-methyl-silyl)-ethoxycarbonyl, or 2-triarylsilylethoxycarbonyl, such as triphenylsilylethoxycarbonyl.

A carboxy group is also protected in the form of an organic silyloxycarbonyl group. An organic silyloxycarbonyl group is, for example, a tri-lower alkylsilyloxycarbonyl group, for example trimethylsilyloxycarbonyl or especially tert-butyl-dimethylsilyloxycarbonyl. The silicon atom of the silyloxycarbonyl group may also be substituted by two lower alkyl groups, for example methyl groups, and an amino or carboxy group of a second molecule of a compound to be protected. Compounds having such protecting groups can be prepared, for example, with dimethylchlorosilane as silylating agent.

A carboxy group is also protected in the form of an internal ester with a hydroxy group present in the molecule at a suitable distance, for example in the γ-position, from the carboxy group, that is to say in the form of a lactone, preferably a γ-lactone.

A protected carboxy group is preferably tert-lower alkoxycarbonyl, for example tert-butoxycarbonyl, benzyloxycarbonyl, 4-nitrobenzyloxycarbonyl, 9-fluorenylmethoxycarbonyl or diphenylmethoxycarbonyl, tri-lower alkylsilyloxycarbonyl, for example tert-butyldimethylsilyloxycarbonyl, or a carboxy group protected in the form of a lactone, especially a γ-lactone.

A protected amino group is protected by an amino-protecting group, for example in the form of an acylamino, arylmethylamino, etherified mercaptoamino, 2-acyl-lower alk-1-enylamino or silylamino group or in the form of an azido group.

In an acylamino group, acyl is, for example, the acyl radical of an organic carboxylic acid having, for example, up to 18 carbon atoms, especially a lower alkanecarboxylic acid that is unsubstituted or substituted, for example, by halogen or by aryl, or of a benzoic acid that is unsubstituted or substituted, for example, by halogen, lower alkoxy or by nitro, or preferably of a carbonic acid semiester. Such acyl groups are preferably lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, benzoyl that is unsubstituted or substituted, for example, by halogen, lower alkoxy or by nitro, such as benzoyl, 4-chlorobenzoyl, 4-methoxybenzoyl or 4-nitrobenzoyl, lower alkoxycarbonyl, preferably lower alkoxycarbonyl branched in the 1-position of the lower alkyl radical or suitably substituted in the 1- or 2-position, for example tert-lower alkoxycarbonyl, such as tert-butoxycarbonyl, aryl-lower alkoxycarbonyl, for example arylmethoxycarbonyl having one, two or three aryl radicals that are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(trisubstituted silyl)-lower alkoxycarbonyl, for example 2-tri-lower alkylsilyl-lower alkoxycarbonyl, such as 2-trimethylsilylethoxycarbonyl or 2-(di-n-butyl-methyl-silyl)-ethoxycarbonyl, or triarylsilyl-lower alkoxycarbonyl, for example 2-triphenylsilylethoxycarbonyl.

In an arylmethylamino group, for example a mono-, di- or especially tri-arylmethylamino group, the aryl radicals are especially unsubstituted or substituted phenyl radicals. Such groups are, for example, benzyl-, diphenylmethyl- or especially trityl-amino.

In an etherified mercaptoamino group, the mercapto group is especially in the form of substituted arylthio or aryl-lower alkylthio wherein aryl is, for example, phenyl that is unsubstituted or substituted, for example, by lower alkyl, such as methyl or tert-butyl, lower alkoxy, such as methoxy, halogen, such as chlorine, and/or by nitro, for example in the form of 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester.

Corresponding protecting groups are especially 1-lower alkanoyl-lower alk-1-en-2-yl, for example 1-lower alkanoyl-prop-1-en-2-yl, such as 1-acetyl-prop-1-en-2-yl, or lower alkoxycarbonyl-lower alk-1-en-2-yl, for example lower alkoxycarbonyl-prop-1-en-2-yl, such as 1-ethoxycarbonyl-prop-1-en-2-yl.

A silylamino group is, for example, a tri-lower alkylsilylamino group, for example trimethylsilylamino or tert-butyl-dimethylsilylamino. The silicon atom of the silylamino group can also be substituted by only two lower alkyl groups, for example methyl groups, and by the amino group or carboxy group of a second molecule of formula I. Compounds having such protecting groups can be prepared, for example, using the corresponding chlorosilanes, such as dimethylchlorosilane, as silylating agent.

An amino group can also be protected by conversion into the protonated form; suitable proton donors are, especially, strong inorganic acids, such as sulfuric acid, phosphoric acid or hydrohalic acids, for example hydrochloric or hydrobromic acid, or organic sulfonic acids, such as p-toluenesulfonic acid.

Preferred amino-protecting groups are lower alkoxycarbonyl, phenyl-lower alkoxycarbonyl, 9-fluorenyl-lower alkoxycarbonyl, 2-lower alkanoyl-lower alk-1-en-2-yl or lower alkoxycarbonyl-lower alk-1-en-2-yl, more especially tert-butoxycarbonyl or benzyloxycarbonyl.

For the protection of imino groups it is possible to use all the mentioned monovalent amino-protecting groups and, where chemically possible, also divalent amino-protecting groups.

A hydroxy group can be protected, for example, by an acyl group, for example by halo-substituted, such as chloro-substituted, lower alkanoyl, such as 2,2-dichloroacetyl, or especially by an acyl radical of a carbonic acid semiester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A hydroxy group may also be protected by tri-lower alkylsilyl, for example trimethylsilyl, triisopropylsilyl or especially tert-butyl-dimethylsilyl, a readily removable etherifying group, for example an alkyl group, such as tert-lower alkyl, for example tert-butyl, an oxa- or thia-aliphatic or oxa- or thia-cycloaliphatic, especially 2-oxa- or 2-thia-aliphatic or 2-oxa- or 2-thia-cycloaliphatic hydrocarbon radical, for example 1-lower alkoxy-lower alkyl or 1-lower alkylthio-lower alkyl, such as methoxymethyl, 1-methoxyethyl, 1-ethoxyethyl, methylthiomethyl, 1-methylthioethyl or 1-ethylthioethyl, or 2-oxa- or 2-thia-cycloalkyl having from 5 to 7 ring atoms, such as 2-tetrahydrofuryl or 2-tetrahydropyranyl, or a corresponding thia analogue, and also by 1-phenyl-lower alkyl, such as benzyl, diphenylmethyl or trityl, it being possible for the phenyl radicals to be substituted, for example, by halogen, for example chlorine, lower alkoxy, for example methoxy, and/or by nitro.

Two hydroxy groups occurring in a molecule, especially two adjacent hydroxy groups, or a hydroxy group and an amino group adjacent to one another can be protected, for example, by bivalent protecting groups, such as a methylene group that is preferably substituted, for example by one or two lower alkyl radicals or by oxo, for example unsubstituted or substituted alkylidene, for example lower alkylidene, such as isopropylidene, cycloalkylidene, such as cyclohexylidene, a carbonyl group or benzylidene.

A hydroxy group in a position adjacent to a carboxy group can be protected by the formation of an internal ester (lactone), especially a γ-lactone.

Preferably a protected hydroxy group is protected by tri-lower alkylsilyl or in the form of a lactone, especially by tert-butyl-dimethylsilyl or in the form of γ-lactone.

A protecting group, for example a carboxy-protecting group, in the context of this Application is expressly to be understood as including a polymeric carrier bonded in a readily removable manner to the functional group, for example a carboxy group, to be protected, as is suitable, for example, for the Merrifield synthesis. Such a suitable polymeric carrier is especially a polystyrene resin weakly crosslinked by copolymerisation with divinylbenzene and carrying bridge members suitable for reversible bonding.

The removal of protecting groups that are not part of the desired end product of formula I, for example carboxy-, amino-, imino- and/or hydroxy-protecting groups, is effected in a manner known per se, for example by means of solvolysis, especially hydrolysis, alcoholysis or acidolysis, or by means of reduction, especially hydrogenolysis or by means of other reducing agents, and also photolysis, optionally stepwise or simultaneously, it also being possible to employ enzymatic methods. The removal of the protecting groups is described, for example, in the standard works mentioned hereinbefore in the section relating to "Protecting groups".

For example, protected carboxy, for example tert-lower alkoxycarbonyl, lower alkoxycarbonyl substituted in the 2-position by a trisubstituted silyl group or in the 1-position by lower alkoxy or by lower alkylthio, or unsubstituted or substituted diphenylmethoxycarbonyl can be convened into free carboxy by treatment with a suitable acid, such as formic acid, hydrochloric acid or trifluoroacetic acid, optionally with the addition of a nucleophilic compound, such as phenol or anisole. Unsubstituted or substituted benzyloxycarbonyl can be freed, for example, by means of hydrogenolysis, that is to say by treatment with hydrogen in the presence of a metallic hydrogenation catalyst, such as a palladium catalyst. Furthermore, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(H) salt, for example chromium(II) chloride, customarily in the presence of a hydrogen-yielding agent that, together with the metal, is capable of generating nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or an alcohol or thiol, with water preferably being added. By treatment with a reducing metal or metal salt, as described above, it is also possible to convert 2-halo-lower alkoxycarbonyl (optionally after conversion of a 2-bromo-lower alkoxycarbonyl group into a corresponding 2-iodo-lower alkoxycarbonyl group) or aroylmethoxycarbonyl into free carboxy. Aroylmethoxycarbonyl can be cleaved also by treatment with a nucleophilic, preferably salt-forming reagent, such as sodium thiophenolate or sodium iodide. 2-(Trisubstituted silyl)-lower alkoxycarbonyl, such as 2-tri-lower alkylsilyl-lower alkoxycarbonyl, can be converted into free carboxy also by treatment with a salt of hydrofluoric acid yielding the fluoride anion, such as an alkali metal fluoride, for example sodium or potassium fluoride, optionally in the presence of a macrocyclic polyether ("crown" ether), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or acid, or a fluoride, as described above. Esterified carboxy can also be freed enzymatically, for example by esterases or suitable peptidases, for example esterified arginine or lysine, such as lysine methyl ester, by means of trypsin. Carboxy protected in the form of an internal ester, such as in the form of γ-lactone, can be freed by hydrolysis in the presence of a hydroxide-containing base, such as an alkaline earth metal hydroxide or especially an alkali metal hydroxide, for example NaOH, KOH or LiOH, especially LiOH, the correspondingly protected hydroxy group being freed at the same time.

A protected amino group is freed in a manner known per se and, in dependence upon the nature of the protecting groups, in various ways, preferably by means of solvolysis or reduction. Lower alkoxycarbonylamino, such as tert-butoxycarbonylamino, can be cleaved in the presence of acids, for example mineral acids, for example a hydrogen halide, such as hydrogen chloride or hydrogen bromide, especially hydrogen bromide, or in the presence of sulfuric or phosphoric acid, preferably hydrogen chloride, in polar solvents, such as water or a carboxylic acid, such as acetic acid, or ethers, preferably cyclic ethers, such as dioxane, and 2-halo-lower alkoxycarbonylamino (optionally after conversion of a 2-bromo-lower alkoxycarbonylamino group into a 2-iodo-lower alkoxycarbonylamino-group), aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can also be cleaved by treatment with a nucleophilic, preferably salt-forming reagent, such as sodium thiophenolate, and 4-nitrobenzyloxycarbonylamino can be cleaved also by treatment with an alkali metal dithionite, for example sodium dithionite. Unsubstituted or substituted diphenylmethoxycarbonylamino, tert-lower alkoxycarbonylamino or 2-(trisubstituted silyl)-lower alkoxycarbonylamino, such as 2-tri-lower alkylsilyl-lower alkoxycarbonylamino, can be freed by treatment with a suitable acid, for example formic or trifluoroacetic acid; unsubstituted or substituted benzyloxycarbonylamino can be freed, for example, by means of hydrogenolysis, that is to say by treatment with hydrogen in the presence of a suitable hydrogenation catalyst, such as a palladium catalyst, preferably in polar solvents, such as di-lower alkyl-lower alkanoylamides, for example dimethylformamide, ethers, such as cyclic ethers, for example dioxane, or alcohols, such as methanol, ethanol or propanol, with methanol being especially preferred; unsubstituted or substituted triarylmethylamino or formylamino can be freed, for example, by treatment with an acid, such as a mineral acid, for example hydrochloric acid, or an organic acid, for example formic, acetic or trifluoroacetic acid, optionally in the presence of water; and an amino group protected in the form of silylamino can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting substitution product. An amino group protected by 2-(trisubstituted silyl)-lower alkoxycarbonyl, such as 2-tri-lower alkylsilyl-lower alkoxycarbonyl, can be converted into the free amino group also by treatment with a salt of hydrofluoric acid yielding fluoride anions, as indicated above in connection with the freeing of a correspondingly protected carboxy group. In the same way, silyl bonded directly to a hetero atom, such as nitrogen, such as trimethylsilyl, can be removed in the presence of fluoride ions.

Imino groups are freed by removing the protecting groups in question in a manner analogous to that described for the amino compounds.

Amino protected in the form of an azido group is converted into free amino, for example, by reduction, for example by catalytic hydrogenation with hydrogen in the presence of a hydrogenation catalyst, such as platinum oxide, palladium, palladium on active carbon or Raney nickel, by reduction by means of mercapto compounds, such as dithiothreitol or mercaptoethanol, or alternatively by treatment with zinc in the presence of an acid, such as acetic acid. The catalytic hydrogenation is preferably carded out in an inert solvent, such as a halogenated hydrocarbon, for example methylene chloride, or alternatively in water or a mixture of water and an organic solvent, such as an alcohol, especially methanol or ethanol, or dioxane, at approximately from 20° C. to 25° C., or with cooling or heating in the range of approximately from 0° to 50° C., at hydrogen pressures of from normal pressure to 5 atm, preferably about 1 atm.

A hydroxy group protected by a suitable acyl group, a tri-lower alkylsilyl group or by unsubstituted or substituted 1-phenyl-lower alkyl is freed analogously to a correspondingly protected amino group. A hydroxy group protected by 2,2-dichloroacetyl is freed, for example, by basic hydrolysis, and a hydroxy group protected by tert-lower alkyl or by a 2-oxa- or 2-thia-aliphatic or 2-oxa- or 2-thia-cycloaliphatic hydrocarbon radical is freed by acidolysis, for example by treatment with a mineral acid or a strong carboxylic acid, for example trifluoroacetic acid. Two hydroxy groups, or an amino group and a hydroxy group adjacent to one another, that are protected together by a bivalent protecting group, preferably, for example, a methylene group mono- or di-substituted by lower alkyl, such as lower alkylidene, for example isopropylidene, cycloalkylidene, for example cyclohexylidene, or benzylidene, can be freed by acidic solvolysis, especially in the presence of a mineral acid or a strong organic acid. A tri-lower alkylsilyl group is likewise removed by acidolysis, for example by a mineral acid, preferably hydrofluoric acid, or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide, or a strong carboxylic acid. 2-Halo-lower alkoxycarbonyl is removed by the above-mentioned reducing agents, for example a reducing metal, such as zinc, reducing metal salts, such as chromium(II) salts, or by sulfur compounds, for example sodium dithionite or preferably sodium sulfide and carbon disulfide.

The temperatures for freeing the protected functional groups are preferably from −80° to 100° C., more especially from −20° to 50° C., for example from 10° to 35° C., such as in the region of room temperature.

Where there are several protected functional groups present, the protecting groups may, if desired, be so chosen that more than one such group can be removed at the same time, for example by acidolysis, such as by treatment with trifluoroacetic acid, or with hydrogen and a hydrogenation catalyst, such as a palladium/carbon catalyst. Conversely, the groups may also be so chosen that they are not all removed at the same time but may be removed in a desired sequence, with the corresponding intermediates being obtained.

Process b) (Condensation to form an amide bond)

In starting materials of formulae IV and V, functional groups, with the exception of groups that are intended to participate in the reaction or do not react or react only slightly under the reaction conditions, are protected independently of one another by protecting groups.

The condensation for the formation of an amide bond can be carded out in a manner known per se, for example as described in standard works, such as "Houben-Weyl, Methoden der organischen Chemie" ("Methods of Organic Chemistry"), 4th Edition, Vol. 15/11 (1974), Vol. IX (1955) Vol. E 11 (1985), Georg Thieme Verlag, Stuttgart, "The Peptides" (E. Gross and J. Meienhofer, Eds.), Vol. 1 and 2, Academic Press, London and New York, 1979/1980, or M. Bodansky, "Principles of Peptide Synthesis", Springer-Verlag, Berlin 1984, or in H.-D. Jakubke and H. Jescheit, "Aminosäuren, Peptide, Proteine" ("Amino acids, Peptides, Proteins"), Verlag Chemie, Weinheim, Deerfield Beach and Basle 1982.

The carboxylic acids of formula V are either in a form having a free carboxy group or are in the form of a reactive derivative thereof, for example in the form of an activated ester derived from the free carboxy compound, in the form of a reactive anhydride, or in the form of a reactive cyclic amide. The reactive derivatives may also be formed in situ and in some cases may only be present in situ.

Activated esters of compounds of formula V having a carboxy group are especially esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example by the anhydride or carbodiimide method; activated N-hydroxy esters method). Internal esters, for example γ-lactones, can also be used.

Anhydrides of acids may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiesters, for example carbonic acid lower alkyl semiesters (obtainable, for example, by treatment of the corresponding acid with chloroformic acid lower alkyl esters or with a 1-lower alkoxy-carbonyl- 2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate or by reaction of N-alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides having five-membered diazacycles of aromatic character, for example amides that can be prepared with suitable carbonyl compounds, such as amides with imidazoles, for example imidazole (obtainable, for example, by treatment of the corresponding acid with N,N'-carbonyldiimidazole; imidazole method), or pyrazoles, for example 3,5-dimethylpyrazole (obtainable, for example, via the acid hydrazide by treatment with acetylacetone; pyrazolide method).

As mentioned, derivatives of carboxylic acids that are used as acylating agents can also be formed in situ and often even exclusively in situ. That method is especially preferred. For example, N,N'-disubstituted amidino esters can be formed in situ by reacting a mixture of the starting material of formula IV and the acid of formula V used as acylating agent, in the presence of a suitable N,N'-disubstituted carbodiimide, for example N,N'-cyclohexylcarbodiimide, for example in the presence of a suitable base, such as triethylamine. In addition, amino or amido esters of the acid used as acylating agent can be formed in the presence of the starting material of formula V to be acylated by reacting a mixture of the corresponding acid and amino starting materials in the presence of an N,N'-disubstituted carbodiimide, for example N,N'-dicyclohexylcarbodiimide, and an N-hydroxyamine or N-hydroxyamide, for example N-hydroxysuccinimide, where appropriate in the presence of a suitable base, for example 4-dimethylamino-pyridine. Moreover, activation in situ can be achieved by reaction with N,N,N',N'-tetraalkyluronium compounds, such as O-benzotriazol-1-yl-N,N,N',N'-tetramethyluronium hexafluorophosphate. Finally, phosphoric acid anhydrides of the carboxylic acids of formula V can be prepared in situ by reacting an alkylphosphoric acid amide, such as hexamethylphosphoric acid triamide, in the presence of a sulfonic acid anhydride, such as 4-toluenesulfonic acid anhydride, with a salt, such as a tetrafluoroborate, for example sodium tetrafluoroborate, or with another derivative of hexamethylphosphoric acid triamide, such as benzotriazol-1-yloxy-tris(dimethylamino)phosphonium hexafluoride, preferably in the presence of a racemisation-reducing additive, such as N-hydroxybenzotriazole.

The amino group of compounds of formula IV participating in the reaction preferably carries at least one reactive hydrogen atom, especially when the carboxy group reacting therewith is in reactive form; it may, however, itself be derivatised, for example by reaction with a phosphite, such as diethylchlorophosphite, 1,2-phenylenechlorophosphite, ethyldichlorophosphite, ethylenechlorophosphite or tetraethylpyrophosphite. A derivative of such a compound having an amino group is also, for example, a carbamic acid halide, the amino group participating in the reaction being substituted by halocarbonyl, for example chlorocarbonyl.

The condensation of a free carboxylic acid with the corresponding amine can be carded out in an especially preferred manner in the presence of one of the following condensation agents: N,N'-disubstituted carbodiimides, for example diethyl-, dipropyl-, N-ethyl-N'-(3-dimethylaminopropyl)-carbodiimide or especially dicyclohexylcarbodiimide, and also suitable carbonyl compounds, for example N,N'-carbonylimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate, and also activated phosphoric acid derivatives, for example diphenylphosphorylazide, diethylphosphoryl cyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate, there optionally being added racemisation-inhibiting substances, such as 1-hydroxybenzotriazole.

The condensation of activated esters, reactive anhydrides or reactive cyclic amides with the corresponding amines, even when they are formed only in situ, is usually carded out in the presence of an organic base, such as simple tri-lower alkylamines, for example triethylamine or tributylamine, or a tri-lower alkylamine having bulky radicals, for example ethyldiisopropylamine, and/or a heterocyclic base, for example pyridine, 4-dimethylaminopyridine or preferably N-methylmorpholine. If desired, in addition a further condensation agent is used, as described for free carboxylic acids.

The condensation of acid anhydrides with amines can be carded out, for example, in the presence of inorganic carbonates, for example ammonium or alkali metal carbonates or hydrogen carbonates, such as sodium or potassium carbonate or hydrogen carbonate (customarily together with a sulfate).

Carboxylic acid chlorides, for example the chlorocarbonic acid derivatives derived from the acid of formula V, are condensed with the corresponding amines preferably in the presence of an organic amine, for example the above-mentioned tri-lower alkylamines or heterocyclic bases, optionally in the presence of a hydrogen sulfate.

In an analogous manner, many of the types of reaction mentioned above for carboxylic acids of formula V can also be employed for compounds of formula V having a terminal sulfonyl group (lower alkanesulfonic acids) in the condensation with compounds of formula V to form sulfonamides.

For example, it is possible to use activated sulfonic acid esters, for example the corresponding aryl esters, especially those substituted by nitro groups, such as phenyl esters, it being possible for the amine component of formula IV also to be used in the form of an alkali metal amide, for example an alkali metal arylamide, such as sodium aniline amide, or an alkali metal salt of a nitrogen-containing heterocycle, for example potassium pyrrolide.

In addition, reactive anhydrides may be used, such as the corresponding symmetric acid anhydrides (which can be prepared, for example, by reaction of the alkanesulfonic acid silver salts with alkanesulfonyl chlorides) or, preferably, the corresponding asymmetric acid anhydrides, for example anhydrides with inorganic acids, such as sulfonyl halides, especially sulfonyl chlorides (obtainable, for example, by reaction of the corresponding sulfonic acids with inorganic acid chlorides, for example thionyl chloride, phosphorus pentachloride), with organic carboxylic acids (obtainable, for example, by treatment of a sulfonic acid halide with the salt of a carboxylic acid, such as an alkali metal salt, analogously to the above-mentioned mixed sulfonic acid anhydrides method), or azides (obtainable, for example, from a corresponding sulfonic acid chloride and sodium azide or via the corresponding hydrazide and treatment thereof with nitrous acid analogously to the above-mentioned azide method).

The condensation is preferably carded out in an inert, aprotic, preferably anhydrous solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately $-40°$ C. to approximately $+100°$ C., preferably from approximately $-10°$ C. to approximately $+50°$ C., and without an inert gas or under an inert gas atmosphere, for example a nitrogen or argon atmosphere.

Aqueous, for example alcoholic solvents; for example ethanol, or aromatic solvents, for example benzene or toluene, are also possible. When alkali metal hydroxides are present as bases it is also possible, optionally, to add acetone.

The condensation can also be effected in accordance with the technique known as solid phase synthesis which is attributed to R. Merrifield and is described, for example, in Angew. Chem. 97, 801–812 (1985), Naturwissenschaften 71, 252–258 (1984) or in R. A. Houghten, Proc. Natl. Acad. Sci. USA 82, 5131–5135 (1985).

The freeing of functional groups protected by protecting groups in the resulting compounds of formula I having protected functions is effected in accordance with one or more of the methods mentioned under Process a).

Process c) (Condensation to form an amide bond)

In starting materials of formulae VI and VII, functional groups, with the exception of groups that are intended to participate in the reaction or do not react or react only slightly under the reaction conditions, are protected independently of one another by protecting groups.

The condensation to form the amide bond with the formation of a compound of formula I in which one or more functional groups may be in protected form, is carried out in a manner analogous to that described under Process b). The corresponding reactive acid derivatives and reactive amino derivatives are also analogous to those described for Process b).

The freeing of functional groups protected by protecting groups in the resulting compounds of formula I having protected functions is effected in accordance with one or more of the methods mentioned under Process a).

Process d) (Condensation to form an amide bond)

In starting materials of formulae VIII and IX, functional groups, with the exception of groups that are intended to participate in the reaction or do not react or react only slightly under the reaction conditions, are protected independently of one another by protecting groups.

The condensation to form the amide bond with the formation of a compound of formula I in which one or more functional groups may be in protected form, is carded out in a manner analogous to that described under Process b). The corresponding reactive acid derivatives and reactive amino derivatives are also analogous to those described for Process b).

The freeing of functional groups protected by protecting groups in the resulting compounds of formula I having protected functions is effected in accordance with one or more of the methods mentioned under Process a).

Process e) (Condensation to form an amide bond)

In starting materials of formulae X and XI, functional groups, with the exception of groups that are intended to participate in the reaction or do not react or react only slightly under the reaction conditions, are protected independently of one another by protecting groups.

The condensation to form the amide bond with the formation of a compound of formula I in which one or more functional groups may be in protected form, is carried out in a manner analogous to that described under Process b). The corresponding reactive acid derivatives are also analogous to those described for Process b), and the reactive imino derivatives of formula IX are analogous to the reactive amino derivatives described under Process b) where this is chemically possible.

The freeing of functional groups protected by protecting groups in the resulting compounds of formula I having protected functions is effected in accordance with one or more of the methods mentioned under Process a).

Additional Process Steps

In the additional process steps, which are optional, functional groups of the starting compounds that are not intended to participate in the reaction may be in unprotected or, if necessary, in protected form, for example they may be protected by one or more of the protecting groups mentioned above under Process a). The protecting groups may be removed all at once or stepwise in accordance with one or more of the methods mentioned under Process a) . Reference is here expressly made to the fact that an amino group can be protected in the form of an azido group and that the freeing of the amino group from the azido group is regarded in the context of this text as being the removal of a protecting group.

Salts of compounds of formula I having at least one salt-forming group may be prepared in a manner known per se. For example, salts of compounds of formula I having acidic groups may be formed, for example, by treatment with metal compounds, such as alkali metal salts of suitable organic carboxylic acids, for example the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, there preferably being used stoichiometric amounts or only a small excess of the salt-forming agent. Acid addition salts of compounds of formula I are obtained in customary manner, for example by treatment with an acid or a suitable anion exchange reagent. Internal salts of compounds of formula I having acidic and basic salt-forming groups, for example a free carboxy group and a free amino group, may be formed, for example, by the neutralisation of salts, such as acid addition salts, to the isoelectric point, for example with weak bases, or by treatment with ion exchangers.

Salts can be converted in customary manner into the free compounds; metal and ammonium salts can be converted, for example, by treatment with suitable acids or acidic ion exchangers, and acid addition salts can be converted, for example, by treatment with a suitable basic agent or basic ion exchangers.

The conversion of a salt of a compound of formula I into a different salt can be effected via the free compound or by direct exchange of the salt-forming ion, for example by ion exchange chromatography.

Stereoisomeric mixtures, that is to say mixtures of diastereoisomers and/or enantiomers, such as, for example, racemic mixtures, can be separated into the corresponding isomers in a manner known per se by suitable separating methods. For example, mixtures of diastereoisomers can be separated into the individual diastereoisomers by fractional crystallisation, chromatography, solvent partition etc. Racemates can be separated from one another, after conversion of the optical antipodes into diastereoisomers, for example by reaction with optically active compounds, for example optically active acids or bases, by chromatography on column materials with optically active compounds or by enzymatic methods, for example by selective reaction of only one of the two enantiomers. This separation can be carried out either at the stage of one of the starting materials or with the compounds of formula I themselves.

In an obtainable compound of formula I, an amino or carboxamide group can be substituted, a carboxy group present in free or reactive form can be esterified or amidated, and an esterified or amidated carboxy group can be converted into a free carboxy group.

The substitution of an amino group by alkylation with the introduction of lower alkyl $R_1$ for the preparation of compounds of formula I wherein $R_2$ is one of the above-mentioned radicals except for hydrogen or lower alkyl, and/or the alkylation of compounds of formula I wherein $R_1$ is piperazinocarbonyl for the preparation of the corresponding N-$C_1$-$C_4$alkyl-piperazino compounds, is effected, for example, by alkylation.

Suitable agents for the alkylation of a compound of formula I are, for example, diazo compounds, for example diazomethane. Diazomethane can be decomposed in an inert solvent, the free methylene that is formed reacting with the carboxamide group in the compound of formula I. The decomposition of diazomethane is preferably effected catalytically, for example in the presence of a noble metal in finely divided form, for example copper, or a noble metal salt, for example copper(I) chloride or copper(II) sulfate.

Alkylating agents are also mentioned in German Offenlegungsschrift 2 331 133, which agents can be reacted under the reaction conditions mentioned therein with a compound of formula I having a carboxamide group.

Further alkylating agents are selected from corresponding lower alkyl compounds that carry an X substituent, wherein X is a leaving group. A leaving group is especially a nucleofugal leaving group selected from hydroxy esterified by a strong inorganic or organic acid, such as hydroxy esterified by a mineral acid, for example a hydrohalic acid, such as hydrochloric, hydrobromic or hydriodic acid, or by a strong organic sulfonic acid, such as a lower alkanesulfonic acid that is unsubstituted or substituted, for example, by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic, trimethanesulfonic or p-toluenesulfonic acid, or hydroxy esterified by hydrazoic acid.

The reaction may take place under the conditions of a nucleophilic substitution of the first or second order, for example as described under Process a).

In an obtainable compound of formula I wherein the substituents $R_1$, $R_2$ and $R_3$ are as defined, $R_4$ is a free hydroxy group and the remaining functional groups are in protected form, the free hydroxy group can be etherified with a $C_1$-$C_4$alkyl radical.

The etherification can be carded out with reagents suitable for the introduction of $C_1$-$C_4$alkyl radicals selected from the above-mentioned alkylating agents, and under the reaction conditions described above, for example with diazomethane, $C_1$-$C_4$alkyl halides, sulfonic acid esters, Meerwein salts, 1-substituted 3-aryltriazenes etc.

In an obtainable compound of formula I, a thio group, for example in thiomorpholinocarbonyl $R_2$ and/or thiomorpholino $R_3$, can be oxidised to a sulfinyl or sulfonyl group, or a sulfinyl group, such as in S-oxo-thiomorpholinocarbonyl $R_2$ and/or S-oxo-thiomorpholino $R_3$, can be oxidised to a sulfonyl group.

The oxidation to the sulfonyl group can be carried out using most of the customary oxidising agents. It is preferable to use those oxidising agents which oxidise the thio group or sulfinyl group selectively in the presence of other functional groups in the compound of formula I, for example the amide function or the hydroxy group, for example aromatic or aliphatic peroxycarboxylic acids, for example perbenzoic acid, monoperphthalic acid, m-chloroperbenzoic acid, peracetic acid, performic acid or trifluoroperacetic acid. The oxidation with peroxycarboxylic acids is effected in the customary solvents suitable for that purpose, for example chlorinated hydrocarbons, for example methylene chloride or chloroform, ethers, such as diethyl ether or dioxane, esters, such as ethyl acetate or the like, at temperatures of from −78° C. to room temperature, for example from −20° C. to +10° C., preferably about 0° C. The peroxycarboxylic acid can also be formed in situ, for example with hydrogen peroxide in acetic acid or formic acid, which optionally contains acetic anhydride, for example with 30% or 90% hydrogen peroxide in acetic acid/acetic anhydride. Other peroxo compounds are also suitable, for example potassium peroxomonosulfate in lower alkanol/water mixtures, for example methanol/water or ethanol/water, or in aqueous acetic acid at temperatures of from −70° C. to +30° C., for example from −20° C. to room temperature, and also sodium metaperiodate in methanol or methanol/water mixtures at temperatures of from 0° C. to 50° C., for example about room temperature.

For the oxidation of the thio group to the sulfinyl group there are used selective oxidising agents in equimolar amounts or in only slight excess under controlled reaction conditions in order to avoid overoxidation to the sulfonyl group. There are suitable, for example, sodium metaperiodate in methanol or methanol/water mixtures at temperatures of from −15° C. to room temperature, for example about 0° C., m-chloroperbenzoic acid in methylene chloride, chloroform or ethyl acetate at temperatures of from −78° C. to 10° C., preferably from −30° C. to 0° C., and also tert-butyl hypochlorite in lower alkanols, for example methanol, or hydrogen peroxide in acetone or acetic acid at temperatures of about 0° C., or the above-mentioned potassium peroxomonosulfate at low temperatures.

In an obtainable compound of formula I having a sulfinyl group, that group can be reduced to a thio group. Preferred are selective reducing agents that do not affect other functional groups in the compound of formula I, for example the amide function. Examples of such selective reducing agents are dichloroborane, which is preferably used in tetrahydrofuran or dimethoxyethane at temperatures of from $-30°$ C. to $+10°$ C., triphenylphosphine in boiling carbon tetrachloride, trichlorosilane or hexachlorodisilane, iron pentacarbonyl, and also sodium hydrogen sulfite in aqueous/alcoholic solvents, for example water/methanol, water/ethanol or water/tetrahydrofuran, at temperatures of from $-10°$ C. to $+50°$ C., and also sodium borohydride in the presence of cobalt(II) chloride or alternatively hydrogen in the presence of catalytic amounts of palladium, for example palladium/carbon in boiling ethanol.

If desired, in an obtainable compound of formula I a sulfonyl group can be reduced to a thio group, for example with diisobutylaluminium hydride in ether or tetrahydrofuran.

The invention relates also to those forms of the process in which a compound obtainable as intermediate at any stage is used as starting material and the remaining steps are carried out or the process is interrupted at any stage or a starting material is formed under the reaction conditions or is used in the form of a reactive derivative or salt, or a compound obtainable according to the process of the invention is produced under the process conditions and processed further in situ. It is preferable to begin with those starting materials which result in the compounds described above as being preferred.

Starting compounds

The present invention relates also to novel starting materials and/or intermediates and to processes for the preparation thereof. The starting materials used and the reaction conditions chosen are preferably those which result in the compounds described as being preferred.

In the preparation of all the starting materials, free functional groups that are not intended to participate in the reaction in question may be in unprotected or protected form, but are preferably protected, especially by the protecting groups mentioned above under Process a). Those protecting groups can be freed at suitable points by the reactions described under Process a). A compound having salt-forming groups can also be used in the form of a salt, provided that the reactions allow it, and salts may at any stage be prepared or converted into the free compounds again.

In the formulae, unless the stereochemistry of asymmetric carbon atoms is defined by the selection of appropriate bond symbols, the asymmetric carbon atoms can be in the (S)-, (R)- or (R,S)-configuration.

The amino compounds of formula II can be prepared according to processes known per se.

For example, they can be prepared from compounds of formula I wherein $R_1$ is hydrogen, $R_2$ is a group removable under the conditions of the protecting group removal methods mentioned under Process a), for example lower alkoxycarbonyl, phenyl- or naphthyl-lower alkoxycarbonyl, and the remaining radicals are as defined, by removing the corresponding radicals $R_2$. The corresponding compounds of formula I can be prepared, for example, in accordance with one of the methods mentioned under Process c), d) or e), the starting compounds for which can be prepared as described below.

The compounds of formula III are known or can be prepared according to processes known per se, or they are commercially available.

The amino compounds of formula IV can be prepared according to processes known per se.

For example, they can be prepared from compounds of formula I wherein $R_2$ is a group removable under the conditions of the protecting group removal methods mentioned under Process a), for example lower alkoxycarbonyl, phenyl- or naphthyl-lower alkoxycarbonyl, and the remaining radicals are as defined, by removing the corresponding radicals $R_2$. The compounds of formula I required for that purpose can be prepared, for example, in accordance with one of the methods mentioned under Process a), c), d) or e); in the case of Process a) a protecting group corresponding to the said removable radicals $R_2$ is present in the protected starting compound of formula II, and in the other processes $R_2$ again has a corresponding definition.

The acids of formula V are known or can be prepared according to processes known per se, or they are commercially available.

Amino compounds of formula VI are known or can be prepared according to processes known per se, for example by peptide synthesis from (D)-, (L)- or (D,L)-valine, (D)-, (L)- or (D,L)-($R_4$-phenyl)alanine and a compound of formula X or corresponding protected derivatives under condensation conditions analogous to those mentioned under Process b).

They are preferably prepared as follows:

A compound of formula XII

(XII)

wherein NProt is a protected amino group, preferably aryl-lower alkoxycarbonylamino, as described under Process a), for example phenyl-lower alkoxycarbonylamino, such as benzyloxycarbonylamino, and $R_4$ is as defined for compounds of formula I, especially the corresponding compound having the (L)-configuration at the asymmetric carbon atom, or a corresponding acid derivative thereof, for example analogous to the acid derivatives described under Process b), is condensed with a compound of formula X under reaction conditions analogous to those mentioned under Process b), preferably in an inert solvent, such as a chlorinated hydrocarbon, for example methylene chloride, at temperatures of from $-80$ to $50°$ C., especially from $-10°$ to $30°$ C., in the presence of a condensation agent, for example a suitable N,N'-disubstituted carbodiimide, for example N,N'-dicyclohexylcarbodiimide (carbodiimide method).

A compound of formula XIII

(XIII)

wherein $R_3$ is as defined for compounds of formula I and the remaining radicals are as defined, is obtained. The freeing of the protecting group at the protected amino group NProt is effected analogously to the conditions mentioned under Process a), preferably in the case of removal of aryl-lower alkoxycarbonyl by catalytic hydrogenation, especially in the presence of noble metal catalysts, such as platinum, rhodium or palladium, optionally in the presence of carder materials, such as silicates, active carbon or aluminium oxides, for example with palladium on active carbon, in polar solvents, for example alcohols, such as methanol or ethanol, at temperatures of from −80° to 50° C., especially from −10° to 30° C.

A compound of formula VIII

wherein the radicals are as defined, is obtained. For the introduction of the radical (L)-, (D)- or (D,L)-valine, the amino compound of formula VIII is condensed with a carboxylic acid of formula XIV

or with a reactive acid derivative thereof, wherein NProt' is a protected amino group, as described above for NProt, under conditions analogous to those described for Process b), preferably under the conditions mentioned for the preparation of formula XIII, and the protecting group is removed as described under Process a), preferably under conditions as described above for the freeing of protecting groups from compounds of formula XIII. A compound of formula VI wherein the radicals are as defined is obtained.

Compounds of formula VII can be prepared according to processes known per se.

The starting material used is preferably the lactone of formula XV

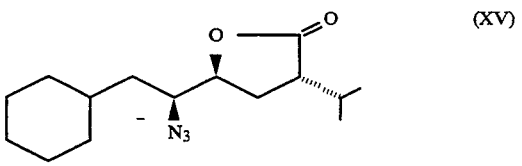

which is prepared in accordance with the process described in J. Org. Chem. 54, 1178–1186 (1989). That compound is hydrolysed, with the lactone being cleaved, preferably in the presence of alkaline compounds, especially hydroxides, for example alkali metal hydroxides, such as sodium hydroxide or potassium hydroxide, in aqueous solvents, for example alcohol/water mixtures, such as methanol/water or ethanol/water, at temperatures of from −80° to 50° C., especially from −10° to 30° C., to form the corresponding free carboxylic acid (5(S)-azido-4(S)-hydroxy-6-cyclohexyl-2(S)-isopropylhexanoic acid) or the corresponding salt, for example the alkali metal salt, such as the sodium salt. The compounds of formula VII are prepared therefrom as follows:

First of all, the carboxy group, in free form or in the form of a salt, and the free hydroxy group are protected with the introduction of one of the protecting groups described under Process a). Preferably, a tri-lower alkylsilyl group, such as tert-butyl-dimethylsilyl, is introduced at the two groups, especially by reaction of 5(S)-azido-4(S)-hydroxy-6-cyclohexyl-2(S)-isopropylhexanoic acid or the corresponding salt, for example an alkali metal salt, such as the sodium salt, with the corresponding tri-lower alkylhalosilane, for example tri-lower alkylchlorosilane, such as tert-butyl-dimethyl-chlorosilane, in the absence or, preferably, the presence of bases, such as cyclic or acyclic nitrogen bases, for example imidazole, in an aprotic solvent, especially a carboxylic acid amide, such as dimethylformamide, at temperatures of from −80° to 50° C., especially from −10° to 30° C., and in the absence or, preferably, the presence of a protective gas, such as nitrogen or argon.

Compounds of formula VII wherein $R_1$ and/or $R_2$ are lower alkyl or hydrogen, but at least one of the two radicals is not hydrogen, can be prepared therefrom by hydrogenating the compound of formula XVI so obtained

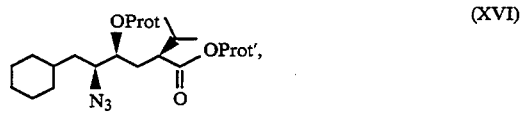

wherein OProt and OProt' are different or, preferably, the same groups selected from those of the mentioned protecting groups which are not removed by hydrogenation, especially one of the mentioned tri-lower alkylsilyl radicals, with reduction of the azide radical, preferably in the presence of a catalyst, for example a noble metal catalyst, such as platinum, rhodium or palladium, which are free or bonded to a carrier, for example to silica gel, aluminium oxide or active carbon, for example palladium on active carbon, in a polar solvent, such as an alcohol for example methanol or ethanol, at temperatures of from −80° to 50° C., especially from −10° to 30° C., under normal pressure or at up to 5 atm hydrogen pressure.

A compound of formula XVII

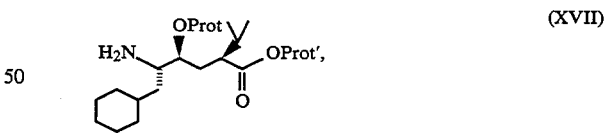

wherein the radicals are as last defined, is obtained. From that compound it is possible to obtain a compound of formula VII directly by removal of the protecting groups OProt and OProt', as described under Process a): carboxy protected in the form of organic silyloxycarbonyl, such as tri-lower alkylsilyloxycarbonyl, for example trimethylsilyloxycarbonyl, is freed in customary manner by solvolysis, for example by treatment with water, an alcohol, a base, especially a carbonate, for example an alkali metal carbonate, such as potassium carbonate, or an acid, or a fluoride, as described under Process a), preferably with an alkali metal carbonate in an aqueous/alcoholic solution, for example methanol or ethanol in water, at temperatures of from −80° to 50° C., especially from −10° to 30° C., under a protective gas, such as argon or nitrogen, while hydroxy protected in the form of organic silyloxy is freed by hydrolysis in the presence of a hydroxide-containing base, such as an alkaline earth metal hydroxide or, preferably, an alkali metal hydroxide, for example NaOH, KOH or LiOH, or by acidolysis, for example by a mineral acid, preferably hydrofluoric acid, or a strong carboxylic acid, or preferably a fluorine salt of an amine, especially tert-butylammonium fluoride in an aprotic polar solvent, for example an acid amide, such as dimethylformamide, at temperatures of from −80° to 50° C., especially from −10° to 30° C. A compound of formula VII wherein $R_1$ and $R_2$ are hydrogen is obtained. Alternatively, the radicals $R_1$ and/or $R_2$, except for hydrogen, can be introduced by alkylation with a compound of formula III, as described under Process a), and/or by acylation with an acid of formula V, as described under Process b), and the protecting groups can be removed only afterwards, there being obtained compounds of formula VII wherein a maximum of one of the radicals $R_1$ and $R_2$ may be hydrogen.

Compounds of formula VIII can be obtained, for example, from compounds of formula XIII, as described above.

Compounds of formula IX can be obtained from carboxylic acids of formula VII or reactive derivatives thereof wherein those functional groups that are not intended to participate in the reaction are protected as described under Process a), by condensation with (D)-, (L)- or (D,L)-valine, wherein the carboxy group is protected as described under Process a), with the formation of an amide bond under the reaction conditions mentioned for Process b), preferably under reaction conditions analogous to those described for the reaction of compounds of formula VIII to form compounds of formula XIV. If necessary, any protecting groups present are removed as described under Process a).

The compounds of formula X are known or can be prepared according to processes known per se, or they are commercially available.

Finally, the compounds of formula XI can be prepared from carboxylic acids of formula IX or reactive derivatives thereof under reaction conditions analogous to the conditions mentioned under Process b), especially those mentioned for the preparation of compounds of formula XI from compounds of formula VII, free functional groups, with the exception of those participating in the reaction, if necessary being present in protected form, and, if necessary, any protecting groups present are removed as described under Process a).

A preferred variant for the preparation of compounds of formula I uses as starting material the compounds of formula VI, prepared as described above from compounds of formulae XIII and XIV, and the compounds of formula XVI prepared as described above, wherein free functional groups, with the exception of those participating in the reaction, are if necessary in protected form, as described under Process a). The carboxy-protecting group. OProt' is removed selectively from a compound of formula XVI, preferably by hydrolysis in the presence of a base, such as a salt of carbonic acid, for example an alkali metal carbonate, such as sodium carbonate, in an aqueous/alcoholic solution, for example in a methanol/water or ethanol/water mixture, at temperatures of from −80° to 50° C., especially from −10° to 30° C., in the absence or, especially, presence of a protective gas, such as nitrogen or argon. A compound of formula XVIII

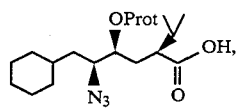

wherein the radicals are as defined for compounds of formula XVI, is obtained. That compound is then condensed with the compound of formula VI under the conditions for the formation of an amide bond, as described under Process b), especially by reaction in situ in the presence of a condensation agent, such as benzotriazol-1-yloxy-tris(dimethylamino)phosphonium hexafluorophosphate, a sterically hindered amine, such as N-methylmorpholine, and a compound inhibiting racemisation, such as 1-hydroxybenzotriazole, in a polar solvent, preferably an acid amide, for example a di-lower alkylamino-lower alkanoylamide, such as dimethylformamide, at temperatures of from −50° to 80° C., especially from 0° to 30° C. The protecting group OProt is removed from the resulting compound, as described for the removal of hydroxy-protecting groups under Process a), especially by hydrolysis in the presence of a hydroxide-containing base, such as an alkaline earth metal hydroxide or especially an alkali metal hydroxide, for example NaOH, KOH or LiOH, or by acidolysis, for example by a mineral acid, preferably hydrofluoric acid, or a strong carboxylic acid, or preferably a fluorine salt of an amine, in an especially preferred manner by tert-butylammonium fluoride in an aprotic polar solvent, for example an acid amide, such as dimethylformamide, at temperatures of from −80° to 50° C., especially from −10° to 30° C. A compound of formula XIX

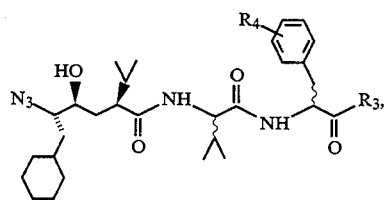

wherein the radicals are as defined for compounds of formula I, is obtained. A compound of formula I wherein $R_1$ and $R_2$ are hydrogen is obtained therefrom by reducing, preferably hydrogenating, the azide group, especially in the presence of a catalyst, for example a noble metal catalyst, such as platinum, rhodium or palladium, which is free or bonded to a carrier, for example to silica gel, aluminium oxide or active carbon, for example palladium on active carbon, in a polar solvent, such as an alcohol, for example methanol or ethanol, at temperatures of from −80° to 50° C., especially from −10° to 30° C., under normal pressure or at up to 5 atm hydrogen pressure.

From the said compound of formula I wherein $R_1$ and $R_2$ are hydrogen there are then prepared, in accordance with Process a) or b) described above, preferably in accordance with Process b), the corresponding compounds of formula I.

General notes on the processes

All the above-mentioned process steps are carded out under reaction conditions known per se, preferably the reaction conditions specifically mentioned, in the absence or, usually, in the presence of solvents or diluents, preferably those solvents or diluents that are inert towards the reagents used and are solvents therefor, in the absence or presence of catalysts, condensation agents or neutralising agents, for example ion exchangers, such as cation exchangers, for example in the OH⁻ or the H⁺ form, and depending upon the nature of the reaction and/or the reactants, at reduced, normal or elevated temperature, for example in a temperature range of from approximately −100° C. to approximately 120° C., preferably from approximately −80° C. to approximately 50° C., especially at from −20° to 40° C., for example from 0° to 25° C., under atmospheric pressure or in a closed vessel, optionally under pressure and/or in an inert atmosphere, for example under an argon or nitrogen atmosphere.

At all stages of the reaction it is possible for any isomeric mixtures which may occur to be separated into the individual isomers, for example diastereoisomers or enantiomers, or into desired mixtures of isomers, for example racemates or diastereoisomers, for example analogously to the methods described under "Additional Process Steps".

The solvents from which the solvents suitable for any particular reaction can be selected include, for example, water, esters, such as lower alkyl-lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, chloroform or tetrachloromethane, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless indicated to the contrary in the description of the processes. Such solvents and solvent mixtures can also be used in-working-up, for example by chromatography or partition. The reaction conditions specific to each of the mentioned reactions are preferred.

Pharmaceutical compositions

The invention relates also to pharmaceutical compositions comprising a compound of formula I as active ingredient.

The pharmacologically acceptable compounds of the present invention may be used, for example, for the preparation of pharmaceutical compositions that comprise an effective amount of the active ingredient together or in admixture with a significant amount of inorganic or organic, solid or liquid, pharmaceutically acceptable carriers.

The pharmaceutical compositions according to the invention are those for enteral, such as nasal, buccal, rectal or oral, or parenteral, such as intramuscular or intravenous, administration to warm-blooded animals (humans and animals), that comprise an effective dose of the pharmacological active ingredient alone or together with a significant amount of a pharmaceutically acceptable carder. The dose of the active ingredient depends upon the species of warm-blooded animal, body weight, age and individual condition, upon individual pharmacokinetic data, the disease to be treated and the mode of administration.

Preferred is a pharmaceutical composition that is suitable for administration to a warm-blooded animal, especially a human, for the treatment or prevention of a disease that responds to inhibitors of retroviral aspartate protease, such as HIV-1- or HIV-2-protease, such as AIDS, comprising an amount of a compound of formula I effective in inhibiting a retroviral aspartate protease, such as HIV-1- or HIV-2-protease, or a salt thereof and one or more carriers.

The invention relates also to a method of treating diseases caused by retroviruses, for example AIDS, especially when HIV-1 causes the disease, which comprises administering an amount of a compound of formula I according to the invention that is therapeutically effective against such diseases, especially to a warm-blooded animal, more especially a human, who on account of one of the mentioned diseases, especially AIDS, requires such treatment. The dose to be administered to warm-blooded animals, especially humans of approximately 70 kg body weight, is preferably from approximately 3 mg to approximately 10 g, especially from approximately 40 mg to approximately 4 g, for example approximately from 300 mg to 1.5 g per person per day, divided preferably into 1 to 3 single doses which may, for example, be of the same size. Children usually receive half of the adult dose.

The pharmaceutical compositions comprise from approximately 1% to approximately 95%, preferably from approximately 20% to approximately 90% active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

It is preferable to use solutions of the active ingredient, and also suspensions, and especially isotonic aqueous solutions or suspensions, it being possible, for example in the case of lyophilised compositions that comprise the active ingredient alone or together with a carrier, for example mannitol, for such solutions or suspensions to be produced prior to use. The pharmaceutical compositions may be sterilised and/or may comprise excipients, for example preservatives, stabilisers, wetting agents and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semisynthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for the active ingredients to be incorporated into plastics carriers that permit the release or diffusion of the active ingredients in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it likewise being possible for stabilisers and/or antibacterial agents to be added. Dyes or pigments may be added to the tablets or dragée coatings or to the capsule casings, for example for identification purposes or to indicate different doses of active ingredient.

The following Examples serve to illustrate the invention but do not limit the scope thereof in any way.

Temperatures are given in degrees Celsius (°C.); the $R_f$ values, which indicate the seepage propagation of the substance in question relative to the propagation of the front edge of the eluant, are determined by thin-layer chromatography (TLC) on silica gel thin-layer plates in the following solvent systems:

TLC eluant systems:

| A: chloroform/methanol/water/acetic acid | (75:27:5:0.5) |
| B: hexane/ethyl acetate | (1:1) |
| C: ethyl acetate | |
| D: methylene chloride/methanol | 9:1 |

The abbreviation "$R_f(A)$" means, for example, that the $R_f$ value has been determined in solvent system A. The quantitative ratio of solvents to one another is always given in proportions by volume (v/v). In the definition of the eluant systems for column chromatography, the quantitative ratios of the solvents used are also given in proportions by volume (v/v).

HPLC systems:

column:

Nucleosil-C18 ® (Macherey & Nagel, Düren), 5µ, 250×4.6 mm, throughflow rate 1 ml/min, detection at 215 nm.

Eluants:

I: 20%→100% acetonitrile/0.1% trifluoroacetic acid in water/0.1% trifluoroacetic acid for 35 min.

II: 0%→40% acetonitrile/0.1% trifluoroacetic acid in water/0.1% trifluoroacetic acid for 30 min.

The other short-forms and abbreviations used have the following meanings:

| atm | physical atmospheres (pressure unit) - 1 atm corresponds to 1.013 bar |
| Boc | tert-butoxycarbonyl |
| BOP | benzotriazol-1-yloxy-tris(di-methylamino)phosphonium hexafluorophosphate |
| brine | saturated sodium chloride solution |
| Cha | cyclohexylalanine |
| DCC | dicyclohexylcarbodiimide |
| DMF | dimethylformamide |
| ether | diethyl ether |
| FAB-MS | Fast-Atom-Bombardment mass spectroscopy |
| HOBt | 1-hydroxybenzotriazole |
| min | minute(s) |
| Pd/C | palladium on active carbon (catalyst) |
| TBAF | tetrabutylammonium fluoride (trihydrate) |
| TLC | thin-layer chromatography |
| $t_{RET}$ | retention time |
| Z | benzyloxycarbonyl |

Mass-spectroscopic measuring values are obtained by the "Fast-Atom-Bombardment" (FAB-MS) method. The mass data relate to the protonated molecule ion $(M+H)^+$.

The abbreviations customary in peptide chemistry are used for naming bivalent radicals of natural α-amino acids. The configuration at the α-carbon atom is indicated by the prefix (L)- or (D)-.

The bivalent radical of 5(S)-amino-6-cyclohexyl-4(S)-hydroxy-2(S)-isopropyl-hexanoic acid has the formula

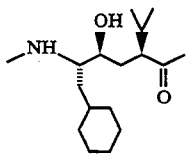

EXAMPLE 1

5(S)-Boc-amino-6-cyclohexyl-4(S)-hydroxy-2(S)-isopropylhexanoyl-(L)-valyl-(L)-phenylalanyl-morpholin-4-ylamide 100 mg (0.17 mmol) of 5(S)-amino-6-cyclohexyl-4(S)-hydroxy-2(S)-isopropyl-hexanoyl-(L)-valyl-(L)-phenylalanyl-morpholin-4-ylamide are dissolved in 5 ml of THF/water (1:1) and at room temperature 62 mg (0.28 mmol) of di-tert-butyl dicarbonate are added. After 2 hours the solvent is evaporated off and the residue is dissolved in ethyl acetate and washed in succession with saturated sodium hydrogen carbonate solution, water and brine. The organic extracts are washed with water and brine, dried over sodium sulfate and concentrated by evaporation. Chromatography of the crude product on silica gel with hexane/ethyl acetate (1:1) yields the title compound in the form of an amorphous solid. FAB-MS: $(M+H)^+=687$, $t_{Ret}(I)=24.7$ rain, TLC $R_f(A)=0.78$.

The starting material is prepared as follows:

1a)
5(S)-Amino-6-cyclohexyl-4(S)-hydroxy-2(S)-isopropyl-hexanoyl-(L)-valyl-(L)-phenylalanyl(morpholin-4-yl)-amide A solution of 387 mg (0.63 mmol) of 5(S)-azido-6-cyclohexyl-4(S)-hydroxy-2(S)-isopropyl-hexanoyl-(L)-Val-(L)-Phe-morpholin-4-ylamide in 40 ml of methanol is hydrogenated for 3.5 hours in the presence of 100 mg of 10% Pd/C at room temperature and 1 atm hydrogen pressure. The catalyst is filtered off and the filtrate is concentrated by evaporation and, after purification by chromatography on silica gel with methylene chloride/methanol/conc. ammonia (90:10:0.1), yields the title compound in the form of an amorphous solid. FAB-MS:$(M+H)^+=587$, $t_{Ret}(I)=14.6$ min, TLC $R_f(A)=0.54$.

1b)
5(S)-Azido-6-cyclohexyl-4(S)-hydroxy-2(S)-isopropyl-hexanoyl-(L)-Val-(L)-Phe-morpholin-4-ylamide 459 mg (1.57 mmol) of TBAF are added to a solution of 570 mg (0.78 mmol) of 5(S)-azido-4(S)-(tert-butyl-dimethylsilyloxy)-6-cyclohexyl-2(S)-isopropyl-hexanoyl(L)-Val-(L)-Phe-morpholin-4-ylamide in 7 ml of DMF and the mixture is stirred at room temperature for 16 hours. The reaction mixture is diluted with water and extracted three times with ethyl acetate. The organic extracts are washed three times with water, twice with saturated sodium hydrogen carbonate solution and once with brine, dried over sodium sulfate and concentrated by evaporation. The crude product is digested with hexane and yields the title compound. FAB-MS: $(M+H)^+=613$, $t_{Ret}(I)=24.7$ min, TLC $R_f(B)=0.15$.

1c)
5(S)-Azido-4(S)-(tert-butyldimethylsilyloxy)-6-cyclohexyl-2(S)-isopropylhexanoyl-(L)-Val-(L)-Phe-morpholin-4-ylamide 487 mg (1.2 mmol) of BOP, 149 mg (1.1 mmol) of HOBt and 330 μl (3 mmol) of N-methylmorpholine are added to a solution of 412 mg (1 mmol) of 5(S)-azido-4(S)-(tert-butyldimethylsilyloxy)-6-cyclohexyl-2(S)-isopropyl-hexanoic acid in 4 ml of DMF (Example 1h) and the mixture is stirred at room temperature for 30 minutes. Then a solution of 400 mg (1.2 mmol) of H-(L)-Val-(L)-Phe-morpholin-4-ylamide (Example 1 g)) in 3 ml of DMF is added. After 2.5 hours the reaction mixture is diluted with water and extracted three times with ethyl acetate. The organic extracts are washed with saturated sodium hydrogen carbonate solution, water and saturated sodium chloride solution, dried over sodium sulfate and concentrated by evaporation. Purification by chromatography on silica gel with a gradient hexane/ethyl acetate (3:1→1:1) yields the title compound in the form of a solidified foam. FAB-MS: $(M+H)^+=727$, $t_{Ret}(I)=37.8$ min, TLC $R_f(B)=0.40$.

1d) Z-(L)-Phe-morpholin-4-ylamide

A solution of 4.49 g of Z-(L)-Phe-OH in 190 ml of methylene chloride is cooled to 0° C. and 3.09 g of DCC are added. After stirring for 20 minutes at 0° C., a solution of 1.31 ml of morpholine in 10 ml of methylene chloride is added dropwise thereto over a period of 15 minutes. The reaction mixture is stirred for a further 24 hours at room temperature and, after the precipitated dicyclohexylurea has been filtered off, is washed in succession with methylene chloride, aqueous sodium hydrogen carbonate solution and brine. Drying over sodium sulfate and concentration yield the crude title compound which crystallises from ether. TLC $R_f(C)=0.55$.

1e) H-(L)-Phe-morpholin-4-ylamide

A solution of 5.5 g of Z-(L)-Phe-morpholin-4-ylamide in 150 ml of methanol is converted into the title compound by hydrogenolysis with the calculated amount of hydrogen for 1 hour at room temperature in the presence of 1.5 g of 10% Pd/C. The catalyst is filtered off and the reaction mixture is concentrated, and after dilution with ethyl acetate the resulting solution is washed with a saturated sodium hydrogen carbonate solution, dried over sodium sulfate and concentrated under reduced pressure. After column chromatography (analogously to Example 1 g)) the title compound is obtained in pure form. TLC $R_f(D)=0.3$.

1f) Z-(L)-Val-(L)-Phe-morpholin-4-ylamide 1.75 g of DCC are added to a solution of 2.14 g of Z-(L)-Val-OH in 80 ml of absolute ice-cooled methylene chloride and after stirring for 20 minutes at that temperature a solution of 2 g of H-(L)-Phe-morpholin-4-ylamide is added dropwise thereto over a period of 15 minutes. The reaction mixture is stirred for a further 24 hours at room temperature and the urea that forms is filtered off. The filtrate is washed in succession with aqueous sodium hydrogen carbonate solution and brine and, after drying over sodium sulfate, concentrated. Stirring with ether and removal of the insoluble residue by filtration yields, after concentration, the title compound which is processed further without additional purification. TLC $R_f(D)=0.7$.

1g) H-(L)-Val-(L)-Phe-morpholin-4-ylamide

In a manner analogous to Example 1 e), 3.9 g of Z-(L)-Val-(L)-Phe-morpholin-4-ylamide in 150 ml of methanol are converted by hydrogenolysis over 0.5 g of 10% Pd/C into the crude title compound, which is purified by column chromatography ($SiO_2$, methylene chloride→methylene chloride/methanol: 97.5 to 2.5 (v/v)). TLC $R_f(D)=0.4$.

1h) 5(S)-Azido-4(S)-(tert-butyldimethylsilyloxy)-6-cyclohexyl-2(S)-isopropylhexanoic acid 11.5 g (168.9 mmol) of imidazole and 13.4 g (88.9 mmol) of tert-butyldimethylchlorosilane are added in succession to a suspension of 11.5 g (35.8 mmol) of the sodium salt of 5(S)-azido-4(S)-hydroxy-6-cyclohexyl-2(S)-isopropyl-hexanoic acid (Example 1i)) in 45 ml of DMF and the mixture is stirred under a nitrogen atmosphere at room temperature for 3.75 days. The reaction mixture is poured onto 500 ml of ice-water and extracted with 4×250 ml of ice-cold hexane. The hexane phase is washed twice each with water and brine, dried over sodium sulfate and concentrated by evaporation. After drying under a high vacuum until the weight is constant, crude 5(S)-azido-4(S)-(tert-butyldimethylsilyloxy)-6-cyclohexyl-2(S)-isopropyl-hexanoic acid tert-butyldimethylsilyl ester is obtained in the form of a light-yellow oil. 10.1 g (17.9 mmol) of that crude product are dissolved in 250 ml of methanol and at 0° C. a solution of 2.72 g (19.7 mmol) of potassium carbonate in 26 ml of water is added; the resulting emulsion is stirred for 2 hours at room temperature under an argon atmosphere. The reaction mixture is concentrated under reduced pressure, diluted with ethyl acetate and ice-cold brine, and the pH value of the aqueous phase is adjusted to 2 with 0.5M potassium hydrogen sulfate solution. The separated aqueous phase is extracted a further three times with ethyl acetate. The combined organic extracts are washed with ice-cold water and ice-cold brine, dried over sodium sulfate and concentrated by evaporation. The crude product consists of a mixture of 76.5% title compound and 23.5% 2(R)-epimer. The diastereoisomeric title compound is obtained after purification by chromatography on a column of silica gel with a gradient of methylene chloride→10% methanol in methylene chloride. $t_{Ret}(I)=37.1$ min, TLC $R_f(B)=0.27$.

1i) Sodium salt of 5(S)-azido-4(S)-hydroxy-6-cyclohexyl-2(S)-isopropyl-hexanoic acid 3.6 ml (3.6 mmol) of 1N sodium hydroxide solution are added at 0° C. to solution of 1 g (3.6 mmol) of (2S,4S,5S)-5-azido-6-cyclohexyl-2-isopropyl-4(S)-hydroxy-hexanoic acid γ-lactone (=(2S,4S,5S)-5-azido-6-cyclohexyl-2-isopropyl-hexanolide) (J. Org. Chem. 54, 1178, (1989)) in 30 ml of methanol and 10 ml of water and the mixture is stirred at room temperature for 15 hours. The reaction mixture is completely concentrated by evaporation, and then methanol, hexane and methylene chloride are each twice added to the residue and completely concentrated by evaporation again. In this manner the title compound is obtained in the form of a crude product which is not subjected to further purification. $t_{Ret}(I)=22.9$ min, TLC $R_f(D)=0.61$.

EXAMPLE 2

5(S)-Amino-6-cyclohexyl-4(S)-hydroxy-2(S)-isopropyl-hexanoyl-(L)-valyl-(L)-phenylalanyl-(thiomorpholin-4-yl)-amide Starting from thiomorpholine instead of morpholine, the title compound is prepared analogously to the process described in Example 1 via intermediate compounds analogous to Examples 1a) to 1i).

EXAMPLE 3

Gelatin solution

A sterile-filtered aqueous solution of the compound of formula I mentioned in Example 1 or 2 above, which additionally comprises 20% cyclodextrin, and a sterile gelatin solution preserved with phenol are mixed together with heating under aseptic conditions in such a manner that 1.0 ml of solution having the following composition is obtained:

| | |
|---|---|
| active ingredient | 3 mg |
| gelatin | 150.0 mg |
| phenol | 4.7 mg |
| dist. water containing 20% cyclodextrins | 1.0 ml |

EXAMPLE 4

Sterile dry substance for injection 5 mg of the compound of formula I mentioned in Example 1 or 2 above, as active ingredient, are dissolved in 1 ml of an aqueous solution containing 20 mg of mannitol and 20% cyclodextrins as solubiliser. The solution is sterile-filtered and under aseptic conditions introduced into a 2 ml ampoule, deep-frozen and lyophilised. Before use, the lyophilisate is dissolved in 1 ml of distilled water or 1 ml of physiological saline solution. The solution is administered intramuscularly or intravenously. This formulation can also be introduced into double-chamber disposable syringes.

EXAMPLE 5

Nasal spray 500 mg of finely ground powder (<5.0 μm) of the compound of formula I mentioned in Example 1 or 2 above, as active ingredient, are suspended in a mixture of 3.5 ml of Myglyol 812 ® and 0.08 μg of benzyl alcohol. That suspension is introduced into a container having a metering valve. 5.0 g of Freon 12 ® are introduced under pressure through the valve into the container. By shaking, the "Freon" is dissolved in the Myglyol/benzyl alcohol mixture.. This spray container contains about 100 single doses which can be administered separately.

EXAMPLE 6

Film-coated tablets

For the preparation of 10 000 tablets each comprising 100 mg of active ingredient, the following constituents are processed:

| | |
|---|---|
| active ingredient | 1000 g |
| corn starch | 680 g |
| colloidal silicic acid | 200 g |
| magnesium stearate | 20 g |
| stearic acid | 50 g |
| sodium carboxymethyl starch | 250 g |

| -continued | |
|---|---|
| water | quantum satis |

A mixture of the compound of formula I mentioned in Example 1 or 2 above, as active ingredient, 50 g of corn starch and colloidal silicic acid is processed into a moist mass with a starch paste consisting of 250 g of corn starch and 2.2 kg of demineralised water. This mass is passed through a sieve of 3 mm mesh size and dried in a fluidised bed drier for 30 minutes at 45°. The dried granules are pressed through a sieve of 1 mm mesh size, mixed with a previously sieved mixture (1 mm sieve) of 330 g of corn starch, the magnesium stearate, the stearic acid and the sodium carboxymethyl starch and compressed to form slightly domed tablets.

What is claimed is:

1. A compound of formula Ib

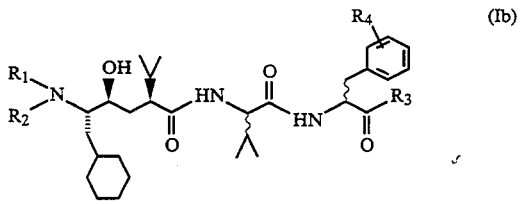

wherein $R_1$ is hydrogen, $R_2$ is lower alkoxycarbonyl, $R_3$ is morpholino and $R_4$ is hydrogen.

2. A compound according to claim 1 formula Ib wherein $R_1$ is hydrogen, $R_2$ is $C_1$–$C_4$alkoxycarbonyl, $R_3$ is morpholino and $R_4$ is hydrogen.

3. A compound according to claim 1 of formula Ib wherein $R_1$ is hydrogen, $R_2$ is tert-butoxycarbonyl, $R_3$ is morpholino and $R_4$ is hydrogen.

4. A pharmaceutical composition suitable for administration to a warm-blooded animal for the treatment or prevention of a disease responsive to the inhibition of HIV aspartate protease, which composition comprises a compound of formula Ib according to claim 1, in an amount effective in inhibiting, HIV aspartate protease, and a pharmaceutically acceptable carrier material.

* * * * *

UNITED STATES PATENT AND TRADEMARK OFFICE
CERTIFICATE OF CORRECTION

Page 1 of 2

PATENT NO. : 5,409,927
DATED : April 25, 1995
INVENTOR(S) : Bold et al.

It is certified that error appears in the above-indentified patent and that said Letters Patent is hereby corrected as shown below:

In column 42, line 5, delete

"

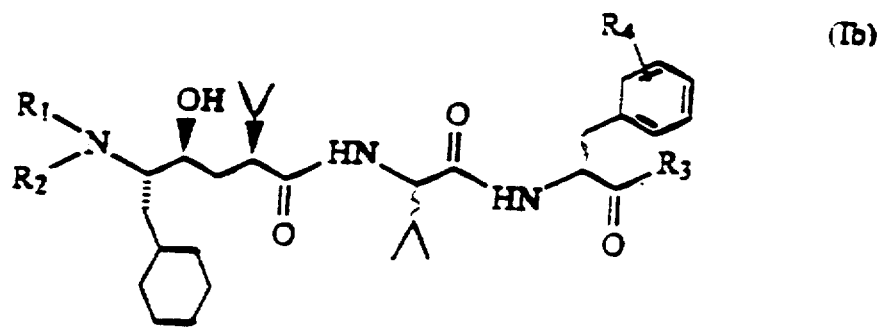

and insert

UNITED STATES PATENT AND TRADEMARK OFFICE
CERTIFICATE OF CORRECTION

PATENT NO. : 5,409,927  
DATED : April 25, 1995  
INVENTOR(S) : Bold et al.

Page 2 of 2

It is certified that error appears in the above-indentified patent and that said Letters Patent is hereby corrected as shown below:

--

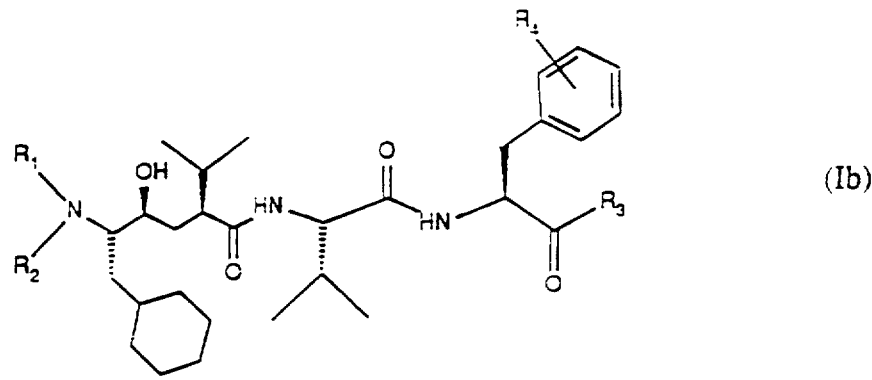

(Ib)

-- in lieu thereof.

Signed and Sealed this

Tenth Day of October, 1995

Attest:

BRUCE LEHMAN

*Attesting Officer*   Commissioner of Patents and Trademarks